(12) United States Patent
Kinney et al.

(10) Patent No.: US 6,730,823 B1
(45) Date of Patent: May 4, 2004

(54) PLANT CHOLINE PHOSPHATE CYTIDYLYLTRANSFERASE

(75) Inventors: Anthony J. Kinney, Wilmington, DE (US); Karlene H. Butler, Newark, DE (US); Kevin L. Stecca, Bear, DE (US); Saverio Carl Falco, Arden, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/735,846

(22) Filed: Dec. 13, 2000

Related U.S. Application Data

(60) Provisional application No. 60/170,375, filed on Dec. 13, 1999.

(51) Int. Cl.$^7$ .......................... A01H 3/00; C07H 21/04; C07K 14/415; C12N 5/14; C12N 9/00

(52) U.S. Cl. .................... 800/278; 435/6; 435/69.1; 435/70.1; 435/183; 435/410; 435/419; 435/252.3; 435/320.1; 530/350; 530/370; 536/23.2; 536/23.6; 536/24.1; 800/295

(58) Field of Search .................. 435/6, 69.1, 70.1, 435/183, 410, 419, 252.3, 320.1; 530/350, 370; 536/23.2, 23.6, 24.1; 800/278, 295

(56) References Cited

PUBLICATIONS

Gabriel B. Kalmar et al., PNAS, vol. 87:6029–6033, Aug. 1990, Cloning and Expression of Rat Liver CTP:phsophocholine Cytidylyltransferase: An Amphipathic Protein that Controls Phosphatidylcholine Synthesis.

Yuko Tsukagoshi et al., Eur. J. Biochem., vol. 169:477–486, 1987, Molecular Cloning and Characterization of the Gene Encoding Cholinephosphate Cytidylytransferase in *Saccharomyces Cerevisiae*.

Philippa L. Jones et al., Plant Molecular Biology, vol. 37:179–185, 1998, Isolation, Characterisation and Expression of a cDNA for Pea Cholinephsophate Cytidylytransferase.

Ikuo Nishida et al., Plant Molecular Biology, vol. 31:205–211, 1996, Cloning of *Brassica Napus* CTP:phsphocholine Cytidylytransferase cDNAs by complementation in a Yeast CCT Mutant.

Wang and Moore, Plant Phys., vol. 96(suppl):126, 1991, Isolation and Characterization of a cDNA Clone Encoding Cholinephosphate Cytidylytransferase from Castor Bean Endosperm.

National Center for Biotechnology Information General Identifier No. 1657382, May 27, 1998, Jones, P.L. et al., Isolation, Characterisation and Expression of a cDNA for Pea Cholinephosphate Cytidylytransferase.

National Center for Biotechnology Information General Identifier No. 1418125, Feb. 12, 1999, Nishida, I. et al., Cloning of *Brassica Napus* CTP:phsphocholine Cytidylyltransferase cDNAs by Complimentation of the in a yeast mutant.

National Center for Biotechnology Information General Identifier No. 1418127, Feb. 13, 1999, Nishida, I. et al., Cloning of *Brassica Napus* CTP:phsphocholine Cytidylyltransferase cDNAs by Complimentation of the in a yeast mutant.

National Center for Biotechnology Information 1416514, Feb. 13, 1999, nishida, i. et al., Cloning of *Brassica Napus* CTP:phsphocholine Cytidylyltransferase cDNAs by Complimentation of the in a yeast mutant.

National Center for a Biotechnology Information General Indentifier No. 7488791, Jul. 21, 2000, Jones, P.L. et al., Isolation, Characterisation and Expression of a cDNA for Pea Cholinephsophate Cytidylytransferase.

National Center for Biotechnology Information General Identifier No. 7488484, May 11, 2000, Nishida, I. et al., Cloning of *Brassica Napus* CTP:phsphocholine Cytidylyltransferase cDNAs by Complimentation of the in a yeast mutant.

National Center for Biotechnology Information General Identifier No. 7488483, May 11, 2000, Nishida, I. et al., Cloning of *Brassica Napus* CTP:phsphocholine Cytidylyltransferase cDNAs by Complimentation of the in a yeast mutant.

National Center for Biotechnology Information General Identifier No. 7488486, Jun. 20, 2000, Fowler, A.

National Center for Biotechnology Information General Identifier No. 4874508, May 19, 1999, Walbot, V., Maize ESTs from Various cDNA Libraries Sequenced at Stanford University.

National Center for Biotechnology Information General Identifier No. 5004923, Jun. 7, 1999, Sasaki, T. et al., Rice cDNA from Immature Leaf Including Apical Meristem.

National Center for Biotechnology Information General Identifier No. 5871198, Sep. 13, 1999, Walbot, V., Maize ESTs from Various cDNA Libraries Sequenced at Stanford University.

*Primary Examiner*—Phuong T. Bui

(57) ABSTRACT

This invention relates to an isolated nucleic acid fragment encoding a cholinephosphate cytidylyltransferase. The invention also relates to the construction of a chimeric gene encoding all or a portion of the cholinephosphate cytidylyltransferase, in sense or antisense orientation, wherein expression of the chimeric gene results in production of altered levels of the cholinephosphate cytidylyltransferase in a transformed host cell.

13 Claims, 4 Drawing Sheets

```
                                                                      60
SEQ ID NO:23  ---------------------------------------------TAD----PTADGPSTA
SEQ ID NO:24  MSNV-----------------------------------------TAD----PTTDGPSTA
SEQ ID NO:25  MSNV-----------------------------------------TGD----RNGDGRSTA
SEQ ID NO: 2  MTNV-----------------------------------------------------------
SEQ ID NO: 8  LKSYA-LRSPFPFR--SFSTPHPLPDMADNAKAAAAHAR--PESSQEEEEDWKEAEG----D
SEQ ID NO:12  ---------------------------------------------------------------
SEQ ID NO:14  LKSYA-LRSPFPFR--SFSTPHPLPDMADNAKAAAAHAR--PESSQEEEEDWKEAEG----D
SEQ ID NO:16  ARGLALPGREAELSSSTRQP-STSNPPSPAQIVTIPARKMARVSNAK----KRQGAKPAS
SEQ ID NO:18  HEVLTS-PSPFSLSLSLSLSLPNLLAMADHAAAEA--APQSSQEEEDWKEAEGGDGD
SEQ ID NO:20  NNHVVL------FVEVLRKR-TFWRKSA------YDVCERNCDLFITKE----KKKREKKRR
SEQ ID NO:22  ARGFPSLAPPLP-------EPSRLPLRMADAKAEAARQAQVPQSSQEEEDWKEAEG----D

120
SEQ ID NO:23  VAVSNSTAIQTSPPTD------RPVRVYADGIYDLF HFGH ARSLEQAKKSFPNTYLLVGCCN
SEQ ID NO:24  VAVSGSAAIQASPPTD------RPVRVYADGIYDLF HFGH ARSLEQAKKSFPNTYLLVGCCN
SEQ ID NO:25  VT------ESSPPSD------PPIRVYADGIYDLF HFGH ARSLEQAKMLFPNTYLLVGCCN
SEQ ID NO: 2  VAEVDRAATNGAGEGGVPTDRPIRVYADGIYDLF HFGH AKSLEQAKKSFPNTYLLVGCCN
SEQ ID NO: 8  ---------------------------------------------------------------
SEQ ID NO:12  VAEVDRAATNGAGEGGVPTDRPIRVYADGIYDLF HFGH AKSLEQAKMLFPNTYLLVGCCN
SEQ ID NO:14  ALSSTDTSTAAKRKAE--DDRPVRVRYADGIFDLF HFGH ARALEQAKMLFPNTYLLVGCCN
SEQ ID NO:16  ---------------GIEFDLF HFGH ARALEQAKLLFPNTYLLVGCCN
SEQ ID NO:18  VEVADRGGGGGAANGGIPEGRPIRVYADGIYDLF HFGH AKSLEQAKRLFPNTYLLVGCCN
SEQ ID NO:20  MADQSEHSKTASPPED--QDRPVRVYADGIYDLF HFGH ARSLEQAKKSFPNTYLLVGCCN
SEQ ID NO:22  VEVADRSTSNGGGAGEGITDRPIRVYADGIYDLF HFGH ARSLEQAKKSFPNAYLLVGCCN
              ** ********** *** **** *************************
```

FIG. 1A

```
                  121                                                              180
SEQ ID NO:23      DETTHKYKGRTVMTAEERYESLRHCKWVDEVIPDAPWVINQEFLDNHRIDYVAHDSLPYA
SEQ ID NO:24      DETTHKYKGRTVMTAEERYESLRHCKWVDEVIPDAPWVINQEFLDNHRIDYVAHDSLPYA
SEQ ID NO:25      DDTTHKYKGKTVMNDQERYESLRHCKWVDEVIPDAPWVINQEFLDKHRIAYVAHDALPYA
SEQ ID NO: 2      DELTHKFKGRTVMTEDERYESLRHCKWVDEVIPDAPWVTEEFLDKHNIDFVAHDSLPYA
SEQ ID NO: 8      ------------------------------------------------------------
SEQ ID NO:12      DELTHKFKGRTVMTEDERYESLRHCKWVDEVIPDAPWVTEEFLDKHNIDFVAHDSLPYA
SEQ ID NO:14      DELTYRYKGKTVMTQEERYESLRHCKWVDEVIPDAPWVLTQEFIDKHQIDYVAHDALPYA
SEQ ID NO:16      DELTNRYKGKTVMTQDERYESLRHCKWVDEVIPDAPWVLTQEFIDKHQIDYVAHDALPYA
SEQ ID NO:18      DELTHKYKGRTVMTEDERYESLRHCKWVDEVIPDAPWVTEEFLNKHNIDFVAHDSLPYA
SEQ ID NO:20      DEVTHKYKGKTVMTEDERYESLRHCKWVDEVIPDAPWVTEEFLDKHNIDFVAHDSLPYA
SEQ ID NO:22      DELTHQYKGRTVMTEDERYESLRHCKWVDEVIPDAPWVTEEFLNKHNIDFVAHDSLPYH
                  *  ** *** ****                    ****   ****** * * *  *** **

181                                                              240
SEQ ID NO:23      DTSGAGKDVYEFVKKVGRFKETMRTEGISTSDIIMRIVKDYNQYVMRNLDRGYSREDLGV
SEQ ID NO:24      DTSGAGKDVYEFVKKVGRFKETMRTEGISTSDIIMRIVKDYNQYVMRNLDRGYSREDLGV
SEQ ID NO:25      DASGAGKDVYEFVKKVGRFKETKRTEGISTSDIIMRIVKDYNQYVMRNLDRGYSREDLGV
SEQ ID NO: 2      DASGAGNDVYEHVKKLGKFKETQRTDGISTSDIIMRIVKDYNEYVMRNLARGYTRKDLGV
SEQ ID NO: 8      ---------------------------------------------------YTRKELGV
SEQ ID NO:12      DASGAGNDVYEHVKKLGKFKETQRTDGISTSDIIMRIVKDYNEYVMRNLARGYTRKDLGV
SEQ ID NO:14      DTSGTANDVYEFGKKIGKFKETQRTDGVSTSDLIMRILKDYNQYVMRNLARGYSRKDLGV
SEQ ID NO:16      DTSGAANDVYEFVKKIGKFKETKRTDGVSTSDLIMRILKDYNQYVMRNLXRGYTRKDL--
SEQ ID NO:18      DASGAGNDVYEFVKKLGKFKETQRTDGISTSDIIMRIVKDYNEYVMRNLARGYTRKDLGV
SEQ ID NO:20      DASGAANDVYEFVKSVGRFKETKRTEGISTSDVIMRIVKDYNQYVLRNLDRGYSRNELGV
SEQ ID NO:22      DASGASNDVYEFVKKLGKFKETKRTEGISTSDIIMRIVKDYNEYVMRNLARGYSRNDLGV
                  * *  ** ***   *    *** ** **** *** ****  **  *** *    * **
```

FIG. 1B

```
                241                                                              300
SEQ ID NO:23    SFVKEKRLRVNMRLKKLQERVKEQQEKVGEKIQTVK----MLRNEWVENADRWVAGFLEI
SEQ ID NO:24    SFVKEKRLRVNMRLKKLQERVKEQQEKVGEKIQTVK----MLRNEWVENADRWVAGFLEI
SEQ ID NO:25    SFVKEKRLRVNMRLKKLQEKVKEQQEKVGEKIQTVK----MVRNEWVENADRWVAGFLEM
SEQ ID NO: 2    SYVKEKRLRVNMGLKNLRDRVKQHQEKVGEKWSTVAK----LQEEWVENADRWVAGFLEK
SEQ ID NO: 8    SYVKEKRLRMNNGLKKLQERVKKQQEEVGKKIQTVGKIAGMHPNEWVENADRLVAGFLEM
SEQ ID NO:12    SYVKEKRLRVNMGLKNLRDRVKQHQEKVGEKWSTVAK----LQEEWVENADRWVAGFLEK
SEQ ID NO:14    SYVKEKQLQVNMKINKLRETVKAHQE----KLQTVAKTAGLNHEEWLANADRWVAGFLEK
SEQ ID NO:16    ------------------------------------------------------------
SEQ ID NO:18    SYVKEKRLRVNMGLKNLRDKVKQHQEKVGEKWNTMAK----LQEEWVENADRWVAGFLEK
SEQ ID NO:20    SYVKEKRLRVNRRLKTLQEKVKEHQEKVGEKIQIVAKTAGMHRNEWVENADRWVAGFLEM
SEQ ID NO:22    SYVKEKRLRVNMGLKTLRDKVKQHQEKVGEKWSTVAK----LQEEWVENADRWVVGFLEK
                 * ****  *  **  *      **  ** ** *  **            ********* * ****

301                                                              360
SEQ ID NO:23    FEEGCHKMGTAIRDRIQERLIRQIPRN---RLENGQD---DDTDDQFYEEYFDHDM-----
SEQ ID NO:24    FEEGCHKMGTAIRDSIQERLIRQIPRK---KLENGED---DDTDDQFYEEYFDHDM-----
SEQ ID NO:25    FEEGCHKMGTAIRDRIQEKLMRQESKE---LLEKGQNGQREDTEEQFYEEYFEHDIVDSC
SEQ ID NO: 2    FEEGCHSMGTAIKERIQERLIKAQSSDFGSLLQYDSYDSDEAKEND--------------
SEQ ID NO: 8    FXXXCHKMGTAXRDRIQERLRAQQLKSL---------------------LYDEW------
SEQ ID NO:12    FEEGCHSMGTAIKERIQERLIKAQSSDFGSLLQYDSYDSDEAKEND--------------
SEQ ID NO:14    FEQHCHNMETAIKDRIQERLGKQLSKG----------------------IIAGLVQEP--
SEQ ID NO:16    ------------------------------------------------------------
SEQ ID NO:18    FEEGCHSMGTAIKERI-KAQSRDF-SLLQYDGEDVDEBEDDD------------------
SEQ ID NO:20    FEEGCHKDGTAIRDRIQERLRGQQSRDGPLRLQNGKDDKDDDDEEYYDE-----------
SEQ ID NO:22    FEEGCHSMGTAIKERIQERLKEAQSRDF-SLLQYDSDDFDDFEEED--------------
                *  **    *       *****
```

FIG. 1C

```
              361                                                    395
SEQ ID NO:23  GSDEDEE--ERYYDEEEDVEEEKYKTVKPDAKDDK
SEQ ID NO:24  GSDEDED--ERYYDEEEDVEEE--KSVKKDAQDNK
SEQ ID NO:25  EDNEDDE--EEYYDEIEEQCSSASKALKSN-----
SEQ ID NO: 2  EDEDEDELFEDV----------------------KE
SEQ ID NO: 8  ---------------------------------DDD
SEQ ID NO:12  EDEDEDELFEDV----------------------KE
SEQ ID NO:14  VTA---------------.-----------------
SEQ ID NO:16  ------------------------------------
SEQ ID NO:18  E-------Y--V----------------------RE
SEQ ID NO:20  EDDSDEEYFEEYYDDDELNPQNNGKDEKKE-----
SEQ ID NO:22  DEVAKDAKY--V----------------------KE
```

FIG. 1D

SEQUENCE LISTING

<160> NUMBER OF SEQ ID NOS: 25

<210> SEQ ID NO 1
<211> LENGTH: 1383
<212> TYPE: DNA
<213> ORGANISM: Zea mays

<400> SEQUENCE: 1

| | | | | | |
|---|---|---|---|---|---|
| ccctcaagtc | ctacgcgctc | cgttcccctt | tccctttccg | aagcttctcg | accccccatc | 60 |
| ccctccctga | catggccgac | aacgcgaagg | ccgcggcggc | gcatgcgagg | ccggagtcgt | 120 |
| cgcaggagga | ggaggaggac | tggaaggagg | ccgaggggga | cgtcgccgaa | gtcgaccgcg | 180 |
| ccgccaccaa | tggcgccggc | gagggggggcg | tgcccacaga | caggccgatc | cgggtctacg | 240 |
| ccgacggcat | ctacgacctc | ttccacttcg | gccatgccaa | gtcgctggag | caggccaaga | 300 |
| agtcgtttcc | aaacacatat | cttcttgttg | gatgctgcaa | tgatgagttg | acacataaat | 360 |
| tcaaaggaag | aactgttatg | actgaggatg | agcgatatga | gtcacttcgt | cattgcaagt | 420 |
| gggttgatga | agtcattcca | gatgctccat | gggtggtgac | agaagagttc | ttggataagc | 480 |
| ataacattga | ttttgttgct | catgattctc | tgccgtatgc | tgatgctagt | ggagctggta | 540 |
| acgatgttta | tgaacatgta | aaaaagcttg | gtaagtttaa | ggagactcag | cgcactgatg | 600 |
| ggatatcaac | atcggacatt | ataatgcgga | ttgttaaaga | ttataatgag | tatgttatgc | 660 |
| ggaatctggc | cagggctac | actagaaagg | atcttggtgt | tagttatgtc | aaggaaaaac | 720 |
| gactgcgagt | gaacatggga | cttaaaaacc | tgcgtgacag | agtgaaacag | caccaagaaa | 780 |
| aagtagggga | gaagtggagc | acggttgcaa | aactccagga | gagtgggtg | gaaaatgcag | 840 |
| accgctgggt | ggctggtttc | ttagagaagt | ttgaggaagg | gtgccactca | atggggacag | 900 |
| ccatcaagga | gaggatccag | gagaggctca | tcaaggcaca | atccagcgac | tttggcagcc | 960 |
| tcctacagta | cgacagctac | gattctgatg | aagccaaaga | aaacgacgag | gacgaagacg | 1020 |
| aagatgaact | ctttgaagac | gtcaaggaat | agcacctccg | tacatataca | atggttttgt | 1080 |
| agctgcaaat | tgtgttgtga | gtcagttgcc | tctctctggt | tggtgatctt | tatatatggt | 1140 |
| ctcaaaggta | ggtcaggttg | caatgtttgt | agctgctctt | ggtgtttgtt | caggcaacgc | 1200 |
| atggttgtaa | aagctgtgga | aagactcttg | tgcagtcaag | gatacagatt | ccgatggtta | 1260 |
| cctttgggtt | agaacatata | cggctgtaaa | attggaagtc | gaggtggtta | aaactctaaa | 1320 |
| aaaaaaaaaa | aaaaaaaaaa | aaaaaaaaaa | aaaaaaaaaa | aaaaaaaaaa | aaaaaaaaaa | 1380 |
| aaa | | | | | | 1383 |

<210> SEQ ID NO 2
<211> LENGTH: 349
<212> TYPE: PRT
<213> ORGANISM: Zea mays

<400> SEQUENCE: 2

Leu Lys Ser Tyr Ala Leu Arg Ser Pro Phe Pro Phe Arg Ser Phe Ser
 1               5                  10                  15

Thr Pro His Pro Leu Pro Asp Met ala Asp Asn Ala Lys Ala Ala Ala
            20                  25                  30

Ala His Ala Arg Pro Glu Ser Ser Gln Glu Glu Glu Glu Asp Trp Lys
        35                  40                  45

Glu Ala Glu Gly Asp Val Ala Glu Val Asp Arg Ala Ala Thr Asn Gly
    50                  55                  60

-continued

```
Ala Gly Glu Gly Gly Val Pro Thr Asp Arg Pro Ile Arg Val Tyr Ala
 65                  70                  75                  80

Asp Gly Ile Tyr Asp Leu Phe His Phe Gly His Ala Lys Ser Leu Glu
             85                  90                  95

Gln Ala Lys Lys Ser Phe Pro Asn Thr Tyr Leu Leu Val Gly Cys Cys
            100                 105                 110

Asn Asp Glu Leu Thr His Lys Phe Lys Gly Arg Thr Val Met Thr Glu
        115                 120                 125

Asp Glu Arg Tyr Glu Ser Leu Arg His Cys Lys Trp Val Asp Glu Val
    130                 135                 140

Ile Pro Asp Ala Pro Trp Val Val Thr Glu Glu Phe Leu Asp Lys His
145                 150                 155                 160

Asn Ile Asp Phe Val Ala His Asp Ser Leu Pro Tyr Ala Asp Ala Ser
                165                 170                 175

Gly Ala Gly Asn Asp Val Tyr Glu His Val Lys Lys Leu Gly Lys Phe
            180                 185                 190

Lys Glu Thr Gln Arg Thr Asp Gly Ile Ser Thr Ser Asp Ile Ile Met
        195                 200                 205

Arg Ile Val Lys Asp Tyr Asn Glu Tyr Val Met Arg Asn Leu Ala Arg
    210                 215                 220

Gly Tyr Thr Arg Lys Asp Leu Gly Val Ser Tyr Val Lys Glu Lys Arg
225                 230                 235                 240

Leu Arg Val Asn Met Gly Leu Lys Asn Leu Arg Asp Arg Val Lys Gln
                245                 250                 255

His Gln Glu Lys Val Gly Glu Lys Trp Ser Thr Val Ala Lys Leu Gln
            260                 265                 270

Glu Glu Trp Val Glu Asn Ala Asp Arg Trp Val Ala Gly Phe Leu Glu
        275                 280                 285

Lys Phe Glu Glu Gly Cys His Ser Met Gly Thr Ala Ile Lys Glu Arg
    290                 295                 300

Ile Gln Glu Arg Leu Ile Lys Ala Gln Ser Ser Asp Phe Gly Ser Leu
305                 310                 315                 320

Leu Gln Tyr Asp Ser Tyr Asp Ser Asp Glu Ala Lys Glu Asn Asp Glu
                325                 330                 335

Asp Glu Asp Glu Asp Glu Leu Phe Glu Asp Val Lys Glu
            340                 345
```

<210> SEQ ID NO 3
<211> LENGTH: 572
<212> TYPE: DNA
<213> ORGANISM: Oryza sativa
<220> FEATURE:
<221> NAME/KEY: unsure
<222> LOCATION: (52)
<221> NAME/KEY: unsure
<222> LOCATION: (464)
<221> NAME/KEY: unsure
<222> LOCATION: (466)
<221> NAME/KEY: unsure
<222> LOCATION: (480)
<221> NAME/KEY: unsure
<222> LOCATION: (525)
<221> NAME/KEY: unsure
<222> LOCATION: (548)
<221> NAME/KEY: unsure
<222> LOCATION: (550)
<221> NAME/KEY: unsure
<222> LOCATION: (572)

<400> SEQUENCE: 3

```
gttctaacct cgccttctcc cttctctctc tctctctctc tctctctctc tntctctctc    60
ccgaaccttc tcgccatggc cgaccacgct gcggcggagg cggcgccgca gtcgtcgcag   120
gaggaggagg aggactggaa ggaggccgag ggggagacgg gggacgtcga ggtggcggac   180
aggggcggcg gaggcggcgc cgccaatggg ggaatcccgg aggggaggcc gatccgggtc   240
tacgcggacg gaatctacga tctcttccac ttcggccacg ccaagtcgct cgagcaggcc   300
aagaggctgt ttcctaacac atatctcctt gtcggatgct gcaatgatga gttgacacat   360
aagtacaaag ggagaactgt tatgacagag gatgagcgat atgaatcact tcgtcactgc   420
aagtgggtgg atgaagtcat tcctgatctc catgggtggt aacngngagaa tcttgaatan   480 acataacatt gatttgttca catgatctct gccgtaagct gatcnagtgg agctgggtaa   540
cgatgtcnan aatttgtcaa aaaacttggt an                                 572
```

<210> SEQ ID NO 4
<211> LENGTH: 149
<212> TYPE: PRT
<213> ORGANISM: Oryza sativa
<220> FEATURE:
<221> NAME/KEY: UNSURE
<222> LOCATION: (18)

<400> SEQUENCE: 4

```
Val Leu Thr Ser Pro Ser Pro Phe Ser Leu Ser Leu Ser Leu
 1               5                  10                  15

Ser Xaa Ser Leu Pro Asn Leu Leu Ala Met Ala Asp His Ala Ala Ala
             20                  25                  30

Glu Ala Ala Pro Gln Ser Ser Gln Glu Glu Glu Asp Trp Lys Glu
         35                  40                  45

Ala Glu Gly Gly Asp Gly Asp Val Glu Val Ala Asp Arg Gly Gly Gly
     50                  55                  60

Gly Gly Ala Ala Asn Gly Gly Ile Pro Glu Gly Arg Pro Ile Arg Val
 65                  70                  75                  80

Tyr Ala Asp Gly Ile Tyr Asp Leu Phe His Phe Gly His Ala Lys Ser
                 85                  90                  95

Leu Glu Gln Ala Lys Arg Leu Phe Pro Asn Thr Tyr Leu Leu Val Gly
            100                 105                 110

Cys Cys Asn Asp Glu Leu Thr His Lys Tyr Lys Gly Arg Thr Val Met
        115                 120                 125

Thr Glu Asp Glu Arg Tyr Glu Ser Leu Arg His Cys Lys Trp Val Asp
    130                 135                 140

Glu Val Ile Pro Asp
145
```

<210> SEQ ID NO 5
<211> LENGTH: 584
<212> TYPE: DNA
<213> ORGANISM: Glycine max

<400> SEQUENCE: 5

```
caaaggcaaa actgttatga cagaggccga acgatacgaa tccctgcgcc actgcaaatg    60
ggtggatgaa gttattcctg atgccccttg ggttatcaat caagagtttc ttgacaagca   120
ctacattgac tatgtggctc atgactctct tccttatgct gatgccagtg gtgctgccaa   180
tgatgtttat gaatttgtta atctgttggg gaggtttaag gaaacaaaac ggaccgaagg   240
aatatccacg tccgatgtta taatgaggat tgtcaaagat tataaccaat atgtgctgcg   300
```

-continued

```
gaacttggat cgtgggtact caagaaacga gcttggcgtg agctatgtga aggaaaagcg      360
actgagggtg aatagaaggt tgaaaacatt acaagagaaa gtgaaggaac atcaagaaaa      420
agttggcgaa aagatccaaa ttgttgcaaa gactgctggc atgcatcgga atgagtgggt      480
ggaaaatgct gatcgttggg tagctggttt tctggaaatg tttgaagaag gttgccacaa      540
ggatgggaca gcaattaggg atcgaattca agagaggtta agag                      584
```

```
<210> SEQ ID NO 6
<211> LENGTH: 194
<212> TYPE: PRT
<213> ORGANISM: Glycine max

<400> SEQUENCE: 6
```

Lys Gly Lys Thr Val Met Thr Glu Ala Glu Arg Tyr Glu Ser Leu Arg
 1               5                  10                  15

His Cys Lys Trp Val Asp Glu Val Ile Pro Asp Ala Pro Trp Val Ile
            20                  25                  30

Asn Gln Glu Phe Leu Asp Lys His Tyr Ile Asp Tyr Val Ala His Asp
        35                  40                  45

Ser Leu Pro Tyr Ala Asp Ala Ser Gly Ala Ala Asn Asp Val Tyr Glu
    50                  55                  60

Phe Val Lys Ser Val Gly Arg Phe Lys Glu Thr Lys Arg Thr Glu Gly
65                  70                  75                  80

Ile Ser Thr Ser Asp Val Ile Met Arg Ile Val Lys Asp Tyr Asn Gln
                85                  90                  95

Tyr Val Leu Arg Asn Leu Asp Arg Gly Tyr Ser Arg Asn Glu Leu Gly
            100                 105                 110

Val Ser Tyr Val Lys Glu Lys Arg Leu Arg Val Asn Arg Arg Leu Lys
        115                 120                 125

Thr Leu Gln Glu Lys Val Lys Glu His Gln Glu Lys Val Gly Glu Lys
    130                 135                 140

Ile Gln Ile Val Ala Lys Thr Ala Gly Met His Arg Asn Glu Trp Val
145                 150                 155                 160

Glu Asn Ala Asp Arg Trp Val Ala Gly Phe Leu Glu Met Phe Glu Glu
                165                 170                 175

Gly Cys His Lys Asp Gly Thr Ala Ile Arg Asp Arg Ile Gln Glu Arg
            180                 185                 190

Leu Arg

```
<210> SEQ ID NO 7
<211> LENGTH: 526
<212> TYPE: DNA
<213> ORGANISM: Glycine max
<220> FEATURE:
<221> NAME/KEY: unsure
<222> LOCATION: (210)..(211)
<221> NAME/KEY: unsure
<222> LOCATION: (214)
<221> NAME/KEY: unsure
<222> LOCATION: (238)
<221> NAME/KEY: unsure
<222> LOCATION: (334)
<221> NAME/KEY: unsure
<222> LOCATION: (413)
<221> NAME/KEY: unsure
<222> LOCATION: (439)
<221> NAME/KEY: unsure
<222> LOCATION: (442)
<221> NAME/KEY: unsure
<222> LOCATION: (448)
```

-continued

```
<221> NAME/KEY: unsure
<222> LOCATION: (451)
<221> NAME/KEY: unsure
<222> LOCATION: (462)
<221> NAME/KEY: unsure
<222> LOCATION: (467)
<221> NAME/KEY: unsure
<222> LOCATION: (500)
<221> NAME/KEY: unsure
<222> LOCATION: (505)..(506)
<221> NAME/KEY: unsure
<222> LOCATION: (512)
<221> NAME/KEY: unsure
<222> LOCATION: (522)

<400> SEQUENCE: 7
tatacaagaa aggagctagg tgttagctat gtcaaggaga agaggttgag aatgaacatg      60
ggacttaaaa aattgcagga gagagtgaag aaacaacaag aggaagtagg aaagaagatt    120
caaacggtgg gaaaaatcgc tggaatgcac cctaatgaat gggttgaaaa cgctgatcgg    180
ttggttgctg gatttcttga gatgtttgan naangttgcc acaaaatggg aacagcantc    240
aggaacagaa tacaggaacg attaagggca cagcagctga aatctcttct ttatgatgag    300
tgggatgatg ataatgaatt ctatgatgat gatnaatact acacagccta aagtgacaaa    360
taaactcgtg tgtctagatt tcgaacattc cataaggtaa gctatccttt ccngtaacga    420
caaatggttt aattcgaanc antactanaa nggacaaatg gnttaantcc atacatatgc    480
aatatgggtt gtaaattaan ttggnnattg tncattccta gnttgt                   526

<210> SEQ ID NO 8
<211> LENGTH: 104
<212> TYPE: PRT
<213> ORGANISM: Glycine max
<220> FEATURE:
<221> NAME/KEY: UNSURE
<222> LOCATION: (70)..(71)..(72)
<221> NAME/KEY: UNSURE
<222> LOCATION: (80)

<400> SEQUENCE: 8

Tyr Thr Arg Lys Glu Leu Gly Val Ser Tyr Val Lys Glu Lys Arg Leu
 1               5                  10                  15

Arg Met Asn Met Gly Leu Lys Lys Leu Gln Glu Arg Val Lys Lys Gln
             20                  25                  30

Gln Glu Glu Val Gly Lys Lys Ile Gln Thr Val Gly Lys Ile Ala Gly
         35                  40                  45

Met His Pro Asn Glu Trp Val Glu Asn Ala Asp Arg Leu Val Ala Gly
     50                  55                  60

Phe Leu Glu Met Phe Xaa Xaa Xaa Cys His Lys Met Gly Thr Ala Xaa
 65                  70                  75                  80

Arg Asp Arg Ile Gln Glu Arg Leu Arg Ala Gln Gln Leu Lys Ser Leu
                 85                  90                  95

Leu Tyr Asp Glu Trp Asp Asp Asp
             100

<210> SEQ ID NO 9
<211> LENGTH: 523
<212> TYPE: DNA
<213> ORGANISM: Triticum aestivum
<220> FEATURE:
<221> NAME/KEY: unsure
<222> LOCATION: (338)
<221> NAME/KEY: unsure
<222> LOCATION: (386)
```

<221> NAME/KEY: unsure
<222> LOCATION: (398)
<221> NAME/KEY: unsure
<222> LOCATION: (401)
<221> NAME/KEY: unsure
<222> LOCATION: (447)
<221> NAME/KEY: unsure
<222> LOCATION: (451)
<221> NAME/KEY: unsure
<222> LOCATION: (487)
<221> NAME/KEY: unsure
<222> LOCATION: (490)
<221> NAME/KEY: unsure
<222> LOCATION: (496)

<400> SEQUENCE: 9

```
aaaaccctgc gtgacaaagt gaagcagcac caagaaaaag tagggagaa gtggagtaca      60
gtggcaaaac tccaggaaga gtgggttgaa aacgcagatc gctgggttgt tggttttcta    120
gagaaattcg aggaaggttg ccattcaatg gaactgcca tcaaggaaag aatccaggaa     180
aggctgaagg aggcgcagtc tagggacttc agccttctac aatacgacag tgacgacttt   240
gacgactttg aagaagaaga cgatgaagtt gccaaagatg ccaaatacgt gaaagaatag   300
cgccactgta aaattttacg tcaaagtata atacgggnat gcaatgcatg ttacgatctt   360
catcaaccgc atccttcacc atgtancgtc cctttgantg ngacttcact gtcaaggtaa   420
atctgcgtcc gtgtttgtac ctgtacntga nggtttctag gcagtagcgt accccttgta   480
atactcnacn gtgggnatac actgttattt gggggtacca ttt                     523
```

<210> SEQ ID NO 10
<211> LENGTH: 86
<212> TYPE: PRT
<213> ORGANISM: Triticum aestivum

<400> SEQUENCE: 10

```
Lys Thr Leu Arg Asp Lys Val Lys Gln His Gln Glu Lys Val Gly Glu
  1               5                  10                  15

Lys Trp Ser Thr Val Ala Lys Leu Gln Glu Glu Trp Val Glu Asn Ala
             20                  25                  30

Asp Arg Trp Val Val Gly Phe Leu Glu Lys Phe Glu Glu Gly Cys His
         35                  40                  45

Ser Met Gly Thr Ala Ile Lys Glu Arg Ile Gln Glu Arg Leu Lys Glu
     50                  55                  60

Ala Gln Ser Arg Asp Phe Ser Leu Leu Gln Tyr Asp Ser Asp Asp Phe
 65                  70                  75                  80

Asp Asp Phe Glu Glu Glu
                 85
```

<210> SEQ ID NO 11
<211> LENGTH: 1374
<212> TYPE: DNA
<213> ORGANISM: Zea mays

<400> SEQUENCE: 11

```
gcacgagccc tcaagtccta cgcgctccgt tcccctttcc ctttccgaag cttctcgacc      60
ccccatcccc tccctgacat ggccgacaac gcgaaggccc ggcggcgca tgcgaggccg     120
gagtcgtcgc aggaggagga ggaggactgg aaggaggccg aggggacgt cgccgaagtc     180
gaccgcgccg ccaccaatgg cgccggcgag ggggcgtgc ccacagacag gccgatccgg    240
gtctacgccg acggcatcta cgacctcttc cacttcggcc atgccaagtc gctggagcag   300
```

-continued

```
gccaagaagt cgtttccaaa cacatatctt cttgttggat gctgcaatga tgagttgaca    360
cataaattca aggaagaac tgttatgact gaggatgagc gatatgagtc acttcgtcat     420
tgcaagtggg ttgatgaagt cattccagat gctccatggg tggtgacaga agagttcttg   480
gataagcata acattgattt tgttgctcat gattctctgc cgtatgctga tgctagtgga    540
gctggtaacg atgtttatga acatgtaaaa aagcttggta agtttaagga gactcagcgc    600
actgatggga tatcaacatc ggacattata atgcggattg ttaaagatta taatgagtat    660
gttatgcgga atctggccag gggctacact agaaaggatc ttggtgttag ttatgtcaag    720
gaaaaacgac tgcgagtgaa catgggactt aaaaacctgc gtgacagagt gaaacagcac    780
caagaaaaag taggggagaa gtggagcacg gttgcaaaac tccaggaaga gtgggtggaa    840
aatgcagacc gctgggtggc tggtttctta gagaagtttg aggaagggtg ccactcaatg    900
gggacagcca tcaaggagag gatccaggag aggctcatca aggcacaatc cagcgacttt    960
ggcagcctcc tacagtacga cagctacgat tctgatgaag ccaaagaaaa cgacgaggac   1020
gaagacgaag atgaactctt tgaagacgtc aaggaatagc acctccgtac atatacaatg   1080
gttttgtagc tgcaaattgt gttgtgagtc agttgcctct ctctggttgg tgatctttat   1140
atatggtctc aaaggtaggt caggttgcaa tgtttgtagc tgctcttggt gtttgttcag   1200
gcaacgcatg gttgtaaaag ctgtggaaag actcttgtgc agtcaaggat acagattccg   1260
atggttacct tgggttaga acatatacgg ctgtaaaatt ggaagtcgag gtggttaaaa    1320
ctctgatatc ttgtctgttt ctttcaaaa aaaaaaaaa aaaaaaaaa aaaa             1374
```

<210> SEQ ID NO 12
<211> LENGTH: 349
<212> TYPE: PRT
<213> ORGANISM: Zea mays

<400> SEQUENCE: 12

```
Leu Lys Ser Tyr Ala Leu Arg Ser Pro Phe Pro Phe Arg Ser Phe Ser
  1               5                  10                  15

Thr Pro His Pro Leu Pro Asp Met Ala Asp Asn Ala Lys Ala Ala Ala
             20                  25                  30

Ala His Ala Arg Pro Glu Ser Ser Gln Glu Glu Glu Glu Asp Trp Lys
         35                  40                  45

Glu Ala Glu Gly Asp Val Ala Glu Val Asp Arg Ala Thr Asn Gly
     50                  55                  60

Ala Gly Glu Gly Gly Val Pro Thr Asp Arg Pro Ile Arg Val Tyr Ala
 65                  70                  75                  80

Asp Gly Ile Tyr Asp Leu Phe His Phe Gly His Ala Lys Ser Leu Glu
                 85                  90                  95

Gln Ala Lys Lys Ser Phe Pro Asn Thr Tyr Leu Leu Val Gly Cys Cys
            100                 105                 110

Asn Asp Glu Leu Thr His Lys Phe Lys Gly Arg Thr Val Met Thr Glu
        115                 120                 125

Asp Glu Arg Tyr Glu Ser Leu Arg His Cys Lys Trp Val Asp Glu Val
    130                 135                 140

Ile Pro Asp Ala Pro Trp Val Val Thr Glu Glu Phe Leu Asp Lys His
145                 150                 155                 160

Asn Ile Asp Phe Val Ala His Asp Ser Leu Pro Tyr Ala Asp Ala Ser
                165                 170                 175

Gly Ala Gly Asn Asp Val Tyr Glu His Val Lys Lys Leu Gly Lys Phe
            180                 185                 190
```

-continued

```
Lys Glu Thr Gln Arg Thr Asp Gly Ile Ser Thr Ser Asp Ile Ile Met
        195                 200                 205

Arg Ile Val Lys Asp Tyr Asn Glu Tyr Val Met Arg Asn Leu Ala Arg
        210                 215                 220

Gly Tyr Thr Arg Lys Asp Leu Gly Val Ser Tyr Val Lys Glu Lys Arg
225                 230                 235                 240

Leu Arg Val Asn Met Gly Leu Lys Asn Leu Arg Asp Arg Val Lys Gln
                245                 250                 255

His Gln Glu Lys Val Gly Glu Lys Trp Ser Thr Val Ala Lys Leu Gln
            260                 265                 270

Glu Glu Trp Val Glu Asn Ala Asp Arg Trp Val Ala Gly Phe Leu Glu
        275                 280                 285

Lys Phe Glu Glu Gly Cys His Ser Met Gly Thr Ala Ile Lys Glu Arg
        290                 295                 300

Ile Gln Glu Arg Leu Ile Lys Ala Gln Ser Ser Asp Phe Gly Ser Leu
305                 310                 315                 320

Leu Gln Tyr Asp Ser Tyr Asp Ser Asp Glu Ala Lys Glu Asn Asp Glu
                325                 330                 335

Asp Glu Asp Glu Asp Glu Leu Phe Glu Asp Val Lys Glu
            340                 345
```

<210> SEQ ID NO 13
<211> LENGTH: 1294
<212> TYPE: DNA
<213> ORGANISM: Zea mays

<400> SEQUENCE: 13

```
tgcacgcggc cttgccctcc caggaaggga ggccgaactg agcagttcga ccaggcagcc      60
atccacctcc aaccccccctt cgcctgcgca atcgttacc atcccagcga aaagatggc      120
gcgcgtctcc aatgccaaga agcggcaggg cgccaagccc gcctccgcgc tcagcagcac     180
cgacaccagc accgccgcaa agaggaaggc cgaggacgac cgccccgtgc gcgtctacgc     240
cgacggcatc ttcgatctct ccacttcgg ccacgcccgc gccctcgagc aggccaagat     300
gctgttcccc aacacctatc ttctcgtcgg atgctgcaac gacgagctaa cctaccgcta    360
caagggcaag accgtcatga cccaggaaga gcgatacgaa tccctgcggc actgcaagtg    420
ggttgatgag tcattcctg atgcaccgtg ggttctcaca caggagttta ttgataagca    480
tcagattgac tatgttgctc atgatgcgct gccttatgct gatactagcg gaacagcaaa   540
tgatgtctat gaatttggta aaagagttgg aaaattcaag gaaacaaaaa ggacagacgg   600
ggtttctact tcagatctca taatgaggat cttgaaggac tataaccagt atgtcatgag   660
gaatttagca cggggctact cgaggaaaga tcttggtgtg agctatgtca aggagaaaca   720
attgcaagtt aatatgaaga tcaataaact gcgggagact gtgaaggcac atcaggaaaa   780
gttgcaaaca gtggcaaaga ctgctggttt gaatcatgaa gaatggcttg ctaatgcgga   840
tcgctgggtt gctggtttcc tagagaagtt tgagcaacac tgccacaata tggaaactgc   900
gatcaaggat cggatacagg agaggctagg gaaacagttg agcaaggaa taatcgctgg    960
tcttgtgcag gaaccggtga cagcctaaaa caggtgatgc tgtcaatgaa acgcactgat   1020
gcttttcaga tcatcctccc gatgtggttc tggtgcgagg cttgtaaggg tgcaacgcgg   1080
ttgctgagac gttttaattt tgtggtgcat gtgaactctt cccgtataca aatgtctata   1140
ggagaggcgt ttggtgtttt gggcatcgtc gtgggcgtgt ttctttgtat ctaacgggtt   1200
```

```
agattaacct tttttttgta tcgagattga tgttctttcg tggttataat aataataaat    1260
aataataata ttgtcaaaaa aaaaaaaaaa aaaa                                1294
```

<210> SEQ ID NO 14
<211> LENGTH: 328
<212> TYPE: PRT
<213> ORGANISM: Zea mays

<400> SEQUENCE: 14

```
Ala Arg Gly Leu Ala Leu Pro Gly Arg Glu Ala Glu Leu Ser Ser Ser
 1               5                  10                  15

Thr Arg Gln Pro Ser Thr Ser Asn Pro Pro Ser Pro Ala Gln Ile Val
            20                  25                  30

Thr Ile Pro Ala Arg Lys Met Ala Arg Val Ser Asn Ala Lys Lys Arg
        35                  40                  45

Gln Gly Ala Lys Pro Ala Ser Ala Leu Ser Ser Thr Asp Thr Ser Thr
    50                  55                  60

Ala Ala Lys Arg Lys Ala Glu Asp Asp Arg Pro Val Arg Val Tyr Ala
65                  70                  75                  80

Asp Gly Ile Phe Asp Leu Phe His Phe Gly His Ala Arg Ala Leu Glu
                85                  90                  95

Gln Ala Lys Met Leu Phe Pro Asn Thr Tyr Leu Leu Val Gly Cys Cys
            100                 105                 110

Asn Asp Glu Leu Thr Tyr Arg Tyr Lys Gly Lys Thr Val Met Thr Gln
        115                 120                 125

Glu Glu Arg Tyr Glu Ser Leu Arg His Cys Lys Trp Val Asp Glu Val
    130                 135                 140

Ile Pro Asp Ala Pro Trp Val Leu Thr Gln Glu Phe Ile Asp Lys His
145                 150                 155                 160

Gln Ile Asp Tyr Val Ala His Asp Ala Leu Pro Tyr Ala Asp Thr Ser
                165                 170                 175

Gly Thr Ala Asn Asp Val Tyr Glu Phe Gly Lys Lys Ile Gly Lys Phe
            180                 185                 190

Lys Glu Thr Lys Arg Thr Asp Gly Val Ser Thr Ser Asp Leu Ile Met
        195                 200                 205

Arg Ile Leu Lys Asp Tyr Asn Gln Tyr Val Met Arg Asn Leu Ala Arg
    210                 215                 220

Gly Tyr Ser Arg Lys Asp Leu Gly Val Ser Tyr Val Lys Glu Lys Gln
225                 230                 235                 240

Leu Gln Val Asn Met Lys Ile Asn Lys Leu Arg Glu Thr Val Lys Ala
                245                 250                 255

His Gln Glu Lys Leu Gln Thr Val Ala Lys Thr Ala Gly Leu Asn His
            260                 265                 270

Glu Glu Trp Leu Ala Asn Ala Asp Arg Trp Val Ala Gly Phe Leu Glu
        275                 280                 285

Lys Phe Glu Gln His Cys His Asn Met Glu Thr Ala Ile Lys Asp Arg
    290                 295                 300

Ile Gln Glu Arg Leu Gly Lys Gln Leu Ser Lys Gly Ile Ile Ala Gly
305                 310                 315                 320

Leu Val Gln Glu Pro Val Thr Ala
                325
```

<210> SEQ ID NO 15
<211> LENGTH: 452
<212> TYPE: DNA

<213> ORGANISM: Oryza sativa
<220> FEATURE:
<221> NAME/KEY: unsure
<222> LOCATION: (424)

<400> SEQUENCE: 15

```
ggcatcttcg atctcttcca cttcggccat gcccgcgccc tcgagcaggc caagttgctg      60
ttccccaaca cgtacctgct agtgggctgc tgcaacgacg agctcaccaa ccgctacaag     120
ggcaagaccg tcatgaccca ggatgagcga tacgagtccc ttcgccactg caatgggtt     180
gatgaggtca ttcctgatgc tccatgggtc ctcacgcaag agttcattga caaacatcag     240
attgactatg ttgctcatga tgcactgcct tatgccgata ctagtggagc tgctaatgat     300
gtctatgaat ttgttaaaaa gattggcaaa ttcaaggaaa cgaaacggac agacggtgta     360
tccacatcag acctcataat gaggatattg aaggactaca atcagtatgt catgaggaat     420
ttancacgtg gtacacaaag gaaagattta tg                                    452
```

<210> SEQ ID NO 16
<211> LENGTH: 150
<212> TYPE: PRT
<213> ORGANISM: Oryza sativa
<220> FEATURE:
<221> NAME/KEY: UNSURE
<222> LOCATION: (142)

<400> SEQUENCE: 16

```
Gly Ile Phe Asp Leu Phe His Phe Gly His Ala Arg Ala Leu Glu Gln
  1               5                  10                  15

Ala Lys Leu Leu Phe Pro Asn Thr Tyr Leu Leu Val Gly Cys Cys Asn
                 20                  25                  30

Asp Glu Leu Thr Asn Arg Tyr Lys Gly Lys Thr Val Met Thr Gln Asp
             35                  40                  45

Glu Arg Tyr Glu Ser Leu Arg His Cys Lys Trp Val Asp Glu Val Ile
         50                  55                  60

Pro Asp Ala Pro Trp Val Leu Thr Gln Glu Phe Ile Asp Lys His Gln
 65                  70                  75                  80

Ile Asp Tyr Val Ala His Asp Ala Leu Pro Tyr Ala Asp Thr Ser Gly
                 85                  90                  95

Ala Ala Asn Asp Val Tyr Glu Phe Val Lys Lys Ile Gly Lys Phe Lys
            100                 105                 110

Glu Thr Lys Arg Thr Asp Gly Val Ser Thr Ser Asp Leu Ile Met Arg
        115                 120                 125

Ile Leu Lys Asp Tyr Asn Gln Tyr Val Met Arg Asn Leu Xaa Arg Gly
    130                 135                 140

Tyr Thr Arg Lys Asp Leu
145                 150
```

<210> SEQ ID NO 17
<211> LENGTH: 1358
<212> TYPE: DNA
<213> ORGANISM: Oryza sativa

<400> SEQUENCE: 17

```
gcacgaggtt ctaacctcgc cttctccctt ctctctctct ctctctctct ctctctctct      60
ctctctcccg aaccttctcg ccatggccga ccacgctgcg gcggaggcgg cgccgcagtc     120
gtcgcaggag gaggaggagg actggaagga ggccgagggg ggagacgggg acgtcgaggt     180
ggcggacagg ggcggcggag gcggcgccgc caatggggga atcccggagg ggaggccgat     240
```

-continued

```
ccgggtctac gcggacggaa tctacgatct cttccacttc ggccacgcca agtcgctcga    300
gcaggccaag aggctgtttc ctaacacata tctccttgtc ggatgctgca atgatgagtt    360
gacacataag tacaaaggga gaactgttat gacagaggat gagcgatatg aatcacttcg    420
tcactgcaag tgggtggatg aagtcattcc tgatgctcca tgggtggtaa cggaagaatt    480
cttgaataaa cataacattg attttgttgc acatgattct ctgccgtatg ctgatgctag    540
tggagctggt aacgatgtct atgaatttgt caaaaaactt ggtaaattta aggaaaccca    600
gcgcacagat gggatatcga cgtcagatat tataatgcgg attgttaagg attataatga    660
gtatgttatg cggaacctgg ccagggggta caccagaaag gatcttggtg tcagttacgt    720
taaggaaaaa agactgagag ttaacatggg attaaaaaac ctgcgtgaca agtgaagca    780
gcaccaagaa aaagtagggg agaagtggaa tacaatggcg aaactccagg aagagtgggt    840
ggaaaatgca gatcgatggg ttgctggttt tctggagaag tttgaagaag ctgccactc    900
aatgggaact gccatcaaag agcggatcca agagaggctc aaggcgcaat ccagggattt    960
cagccttcta cagtatgatg gcgaggatgt tgacgaggat gaggacgacg acgaatatgt   1020
cagagaataa tgccaccact gtgaatatac gtcaagtata atatatgtac atgcgctgca   1080
tgtagcagat cttcaatcct tgggcatgtc atgcaccct ctctcttcag gaatggtgaa   1140
cttgtgcccc ccaggttaga ttttggtgct gtgttgtagc aatagcaggt gttttgttta   1200
ggctaagacg caaagtaagc ctgtaaaatc ccctagtcga tggcctgaat ggttatctgg   1260
aagatacaga tatgttcaat tatattttttg tttagcacac aagaacacta tatttcaatt   1320
gactatctac tatatttcaa aaaaaaaaaa aaaaaaa                             1358
```

<210> SEQ ID NO 18
<211> LENGTH: 342
<212> TYPE: PRT
<213> ORGANISM: Oryza sativa

<400> SEQUENCE: 18

```
His Glu Val Leu Thr Ser Pro Ser Pro Phe Ser Leu Ser Leu Ser Leu
  1               5                  10                  15

Ser Leu Ser Leu Ser Leu Pro Asn Leu Leu Ala Met Ala Asp His Ala
                 20                  25                  30

Ala Ala Glu Ala Ala Pro Gln Ser Ser Gln Glu Glu Glu Glu Asp Trp
             35                  40                  45

Lys Glu Ala Glu Gly Gly Asp Gly Asp Val Glu Val Ala Asp Arg Gly
         50                  55                  60

Gly Gly Gly Ala Ala Asn Gly Gly Ile Pro Glu Gly Arg Pro Ile
 65                  70                  75                  80

Arg Val Tyr Ala Asp Gly Ile Tyr Asp Leu Phe His Phe Gly His Ala
                 85                  90                  95

Lys Ser Leu Glu Gln Ala Lys Arg Leu Phe Pro Asn Thr Tyr Leu Leu
            100                 105                 110

Val Gly Cys Cys Asn Asp Glu Leu Thr His Lys Tyr Lys Gly Arg Thr
        115                 120                 125

Val Met Thr Glu Asp Glu Arg Tyr Glu Ser Leu Arg His Cys Lys Trp
    130                 135                 140

Val Asp Glu Val Ile Pro Asp Ala Pro Trp Val Val Thr Glu Glu Phe
145                 150                 155                 160

Leu Asn Lys His Asn Ile Asp Phe Val Ala His Asp Ser Leu Pro Tyr
                165                 170                 175
```

```
Ala Asp Ala Ser Gly Ala Gly Asn Asp Val Tyr Glu Phe Val Lys Lys
            180                 185                 190
Leu Gly Lys Phe Lys Glu Thr Gln Arg Thr Asp Gly Ile Ser Thr Ser
        195                 200                 205
Asp Ile Ile Met Arg Ile Val Lys Asp Tyr Asn Glu Tyr Val Met Arg
    210                 215                 220
Asn Leu Ala Arg Gly Tyr Thr Arg Lys Asp Leu Gly Val Ser Tyr Val
225                 230                 235                 240
Lys Glu Lys Arg Leu Arg Val Asn Met Gly Leu Lys Asn Leu Arg Asp
                245                 250                 255
Lys Val Lys Gln His Gln Glu Lys Val Gly Glu Lys Trp Asn Thr Met
            260                 265                 270
Ala Lys Leu Gln Glu Glu Trp Val Glu Asn Ala Asp Arg Trp Val Ala
        275                 280                 285
Gly Phe Leu Glu Lys Phe Glu Glu Gly Cys His Ser Met Gly Thr Ala
    290                 295                 300
Ile Lys Glu Arg Ile Gln Glu Arg Leu Lys Ala Gln Ser Arg Asp Phe
305                 310                 315                 320
Ser Leu Leu Gln Tyr Asp Gly Glu Asp Val Asp Glu Asp Glu Asp Asp
                325                 330                 335
Asp Glu Tyr Val Arg Glu
            340

<210> SEQ ID NO 19
<211> LENGTH: 1494
<212> TYPE: DNA
<213> ORGANISM: Glycine max
<220> FEATURE:
<221> NAME/KEY: unsure
<222> LOCATION: (1445)

<400> SEQUENCE: 19
ggcacgaggc taaaaccat ttttttaaga gaaaaacata gtatactctg aaacaatcat      60
gtagtactct tcgtcttcgt tttaagaaaa agaacatttt ggaggaaaag cgcatacgac    120
gtttgcgagc gaaattgcga tttatttatt accaaagaga agaaaaaaag agaaaagaag    180
aggcgaatgg cagatcagag cgagcattcg aaaacggcgt cgcctccgga ggaccaggac    240
cgtcccgttc gagtgtacgc ggatggcatc tacgatctct ccactttgg ccacgctcgc    300
tccctcgagc aagccaagaa atcgtttccg aatacatact tgcttgttgg gtgttgcaac    360
gatgaagtca cccacaaata caaggcaaa actgttatga cagaggccga acgatacgaa    420
tccctgcgcc actgcaaatg ggtggatgaa gttattcctg atgccccttg ggttatcaat    480
caagagtttc ttgacaagca ctacattgac tatgtggctc atgactctct tccttatgct    540
gatgccagtg tgctgccaa tgatgtttat gaatttgtta atctgttgg gaggtttaag    600
gaaacaaaac ggaccgaagg aatatccacg tccgatgtta atgaggat tgtcaaagat    660
tataaccaat atgtgctgcg gaacttggat cgtgggtact caagaaacga gcttggcgtg    720
agctatgtga aggaaaagcg actgagggtg aatagaaggt tgaaaacatt acaagagaaa    780
gtgaaggaac atcaagaaaa agttggcgaa agatccaaa ttgttgcaaa gactgctggc    840
atgcatcgga atgagtgggt ggaaaatgct gatcgttggg tagctggttt tctggaaatg    900
tttgaagaag gttgccacaa ggatgggaca gcaattaggg atcgaattca agagaggtta    960
agaggtcagc agtcaagaga tggaccactt cgtctacaaa atggcaagga tgataaggat   1020
```

-continued

```
gacgatgatg aggagtatta ttatgatgag gaggatgata gtgatgaaga atattttgaa    1080
gaatattatg atgatgatga gcttaatcct caaaataatg aaaagatga gaaaaaagaa    1140 taggtatact tcggtggaat tgttgggttc tcggcagaat gtcaatagca actgtccatg    1200
cgatatctgc aatattatat gcattatgtt ggatagtgga tttgaagttg cccaagggaa    1260
ctttcatttt gctagtgtgg tcaaaatttt acgtgttgaa tgctggtata cgagtgtttg    1320
tgcatatggt taatttaga tgggaaaagt accatatcct ttttattcac ttaattttgg    1380
gttctacatt ctatttcagc gttgctagct cagggaagga aaatcacaaa ttcctcgaac    1440
aatcnaacgt gaattttcac gtcccattga agtcaaaaaa aaaaaaaaaa aaaa           1494
```

<210> SEQ ID NO 20
<211> LENGTH: 363
<212> TYPE: PRT
<213> ORGANISM: Glycine max

<400> SEQUENCE: 20

| Asn | Asn | His | Val | Val | Leu | Phe | Val | Phe | Val | Leu | Arg | Lys | Arg | Thr | Phe |
|---|---|---|---|---|---|---|---|---|---|---|---|---|---|---|---|
| 1 | | | | 5 | | | | | 10 | | | | | 15 | |

| Trp | Arg | Lys | Ser | Ala | Tyr | Asp | Val | Cys | Glu | Arg | Asn | Cys | Asp | Leu | Phe |
| | | | 20 | | | | | 25 | | | | | 30 | | |

| Ile | Thr | Lys | Glu | Lys | Lys | Arg | Glu | Lys | Lys | Arg | Met | Ala | Asp |
| | | 35 | | | | | 40 | | | | | 45 | |

| Gln | Ser | Glu | His | Ser | Lys | Thr | Ala | Ser | Pro | Glu | Asp | Gln | Asp | Arg |
| | 50 | | | | | 55 | | | | | 60 | | | |

| Pro | Val | Arg | Val | Tyr | Ala | Asp | Gly | Ile | Tyr | Asp | Leu | Phe | His | Phe | Gly |
| 65 | | | | | 70 | | | | | 75 | | | | | 80 |

| His | Ala | Arg | Ser | Leu | Glu | Gln | Ala | Lys | Lys | Ser | Phe | Pro | Asn | Thr | Tyr |
| | | | | 85 | | | | | 90 | | | | | 95 | |

| Leu | Leu | Val | Gly | Cys | Cys | Asn | Asp | Glu | Val | Thr | His | Lys | Tyr | Lys | Gly |
| | | | 100 | | | | | 105 | | | | | 110 | | |

| Lys | Thr | Val | Met | Thr | Glu | Ala | Glu | Arg | Tyr | Glu | Ser | Leu | Arg | His | Cys |
| | | | 115 | | | | | 120 | | | | | 125 | | |

| Lys | Trp | Val | Asp | Glu | Val | Ile | Pro | Asp | Ala | Pro | Trp | Val | Ile | Asn | Gln |
| | 130 | | | | | 135 | | | | | 140 | | | | |

| Glu | Phe | Leu | Asp | Lys | His | Tyr | Ile | Asp | Tyr | Val | Ala | His | Asp | Ser | Leu |
| 145 | | | | | 150 | | | | | 155 | | | | | 160 |

| Pro | Tyr | Ala | Asp | Ala | Ser | Gly | Ala | Ala | Asn | Asp | Val | Tyr | Glu | Phe | Val |
| | | | | 165 | | | | | 170 | | | | | 175 | |

| Lys | Ser | Val | Gly | Arg | Phe | Lys | Glu | Thr | Lys | Arg | Thr | Glu | Gly | Ile | Ser |
| | | | 180 | | | | | 185 | | | | | 190 | | |

| Thr | Ser | Asp | Val | Ile | Met | Arg | Ile | Val | Lys | Asp | Tyr | Asn | Gln | Tyr | Val |
| | | 195 | | | | | 200 | | | | | 205 | | | |

| Leu | Arg | Asn | Leu | Asp | Arg | Gly | Tyr | Ser | Arg | Asn | Glu | Leu | Gly | Val | Ser |
| | 210 | | | | | 215 | | | | | 220 | | | | |

| Tyr | Val | Lys | Glu | Lys | Arg | Leu | Arg | Val | Asn | Arg | Arg | Leu | Lys | Thr | Leu |
| 225 | | | | | 230 | | | | | 235 | | | | | 240 |

| Gln | Glu | Lys | Val | Lys | Glu | His | Gln | Lys | Val | Gly | Glu | Lys | Ile | Gln |
| | | | | 245 | | | | | 250 | | | | | 255 |

| Ile | Val | Ala | Lys | Thr | Ala | Gly | Met | His | Arg | Asn | Glu | Trp | Val | Glu | Asn |
| | | | 260 | | | | | 265 | | | | | 270 | | |

| Ala | Asp | Arg | Trp | Val | Ala | Gly | Phe | Leu | Glu | Met | Phe | Glu | Glu | Gly | Cys |
| | | 275 | | | | | 280 | | | | | 285 | | | |

| His | Lys | Asp | Gly | Thr | Ala | Ile | Arg | Asp | Arg | Ile | Gln | Glu | Arg | Leu | Arg |

|     | 290 |     |     | 295 |     |     |     | 300 |     |     |     |
| --- | --- | --- | --- | --- | --- | --- | --- | --- | --- | --- | --- |

Gly Gln Gln Ser Arg Asp Gly Pro Leu Arg Leu Gln Asn Gly Lys Asp
305                 310                 315                 320

Asp Lys Asp Asp Asp Glu Glu Tyr Tyr Tyr Asp Glu Glu Asp
            325                 330                 335

Ser Asp Glu Glu Tyr Phe Glu Gly Tyr Tyr Asp Asp Glu Leu Asn
            340                 345                 350

Pro Gln Asn Asn Gly Lys Asp Glu Lys Lys Glu
            355                 360

<210> SEQ ID NO 21
<211> LENGTH: 1423
<212> TYPE: DNA
<213> ORGANISM: Triticum aestivum

<400> SEQUENCE: 21

```
gcacgaggct tcccgtcgct cgctccccccc ctacccgaac cttctcgact ccctcttcgc    60
atggccgacg cgaaggccga ggcggcgagg caggcgcagg tgccgcagtc ctcccaggag   120
gaggaggagg actggaagga ggccgagggg gacgtcgagg ttgcggacag gtccacgagc   180
aatggcggcg gcgccggcga ggggatcacg gacaggccga tccgggtata cgccgacggc   240
atctacgacc tcttccactt cggccacgcg cgctcgctcg agcaggccaa gaaatcattc   300
cctaatgcat atcttcttgt cgggtgctgc aatgatgagt tgacacatca atacaaagga   360
agaactgtca tgacagagga cgagagatat gaatcacttc gccattgcaa gtgggttgat   420
gaagtcattc ctgacgctcc gtgggtagta acagaagagt tcttgaacaa gcataacatc   480
gattttgttg cacatgattc tctgccgtat catgatgcta gtggagctag taatgatgtc   540
tatgaatttg taaaaagct tggtaaattt aaggagacca gcgcacaga aggaatatca   600
acctcagaca ttataatgag gattgttaaa gattataatg agtatgttat gcgcaatctg   660
gccaggggt acagcagaaa tgatcttggt gtcagctatg tcaaggaaaa acgactaaga   720
gttaatatgg gattgaaaac cctgcgtgac aaagtgaagc agcaccaaga aaagtaggg   780
gagaagtgga gtacagtggc aaaactccag gaagagtggg ttgaaaacgc agatcgctgg   840
gttgttggtt ttctagagaa attcgaggaa ggttgccatt caatgggaac tgccatcaag   900
gaaagaatcc aggaaaggct gaaggaggcg cagtctaggg acttcagcct tctacaatac   960
gacagtgacg actttgacga ctttgaagaa gaagacgatg aagttgccaa agatgccaaa  1020
tacgtgaaag aatagcgcca ctgtaaaatt ttacgtcaaa gtataatacg ggcatgcaat  1080
gcatgttacg atcttcatca accgcaatcc ttcaccatgt atctgtccct ttgattgtga  1140
gcttcactgt caaggtagat ctgcgtgctg tgtttgtagc tgtacttgat ggttttctag  1200
gcagtagcgt acgctcttgt aatagttcta ctgtgaggca taacactgtt tatttggagg  1260
atatcgattt caattcaagt tcttattaag aagtcctgtt ccattctgta actatacttg  1320
tttattttcc attttttgaca tcaaactttg aggaagtgat aaacgactca tcctttgaat  1380
caatggctta ctctacaaaa aaaaaaaaaa aaaaaaaaaa aaa                    1423
```

<210> SEQ ID NO 22
<211> LENGTH: 344
<212> TYPE: PRT
<213> ORGANISM: Triticum aestivum

<400> SEQUENCE: 22

Ala Arg Gly Phe Pro Ser Leu Ala Pro Pro Leu Pro Glu Pro Ser Arg

```
  1               5                   10                  15
Leu Pro Leu Arg Met Ala Asp Ala Lys Ala Glu Ala Ala Arg Gln Ala
                 20                  25                  30

Gln Val Pro Gln Ser Ser Gln Glu Glu Glu Asp Trp Lys Glu Ala
             35                  40                  45

Glu Gly Asp Val Glu Val Ala Asp Arg Ser Thr Ser Asn Gly Gly Gly
         50                  55                  60

Ala Gly Glu Gly Ile Thr Asp Arg Pro Ile Arg Val Tyr Ala Asp Gly
 65                  70                  75                  80

Ile Tyr Asp Leu Phe His Phe Gly His Ala Arg Ser Leu Glu Gln Ala
                 85                  90                  95

Lys Lys Ser Phe Pro Asn Ala Tyr Leu Leu Val Gly Cys Cys Asn Asp
             100                 105                 110

Glu Leu Thr His Gln Tyr Lys Gly Arg Thr Val Met Thr Glu Asp Glu
             115                 120                 125

Arg Tyr Glu Ser Leu Arg His Cys Lys Trp Val Asp Glu Val Ile Pro
 130                 135                 140

Asp Ala Pro Trp Val Val Thr Glu Glu Phe Leu Asn Lys His Asn Ile
145                 150                 155                 160

Asp Phe Val Ala His Asp Ser Leu Pro Tyr His Asp Ala Ser Gly Ala
                 165                 170                 175

Ser Asn Asp Val Tyr Glu Phe Val Lys Lys Leu Gly Lys Phe Lys Glu
             180                 185                 190

Thr Lys Arg Thr Glu Gly Ile Ser Thr Ser Asp Ile Ile Met Arg Ile
             195                 200                 205

Val Lys Asp Tyr Asn Glu Tyr Val Met Arg Asn Leu Ala Arg Gly Tyr
 210                 215                 220

Ser Arg Asn Asp Leu Gly Val Ser Tyr Val Lys Glu Lys Arg Leu Arg
225                 230                 235                 240

Val Asn Met Gly Leu Lys Thr Leu Arg Asp Lys Val Lys Gln His Gln
                 245                 250                 255

Glu Lys Val Gly Glu Lys Trp Ser Thr Val Ala Lys Leu Gln Glu Glu
             260                 265                 270

Trp Val Glu Asn Ala Asp Arg Trp Val Val Gly Phe Leu Glu Lys Phe
             275                 280                 285

Glu Glu Gly Cys His Ser Met Gly Thr Ala Ile Lys Glu Arg Ile Gln
 290                 295                 300

Glu Arg Leu Lys Glu Ala Gln Ser Arg Asp Phe Ser Leu Leu Gln Tyr
305                 310                 315                 320

Asp Ser Asp Asp Phe Asp Phe Glu Glu Glu Asp Glu Val Ala
                 325                 330                 335

Lys Asp Ala Lys Tyr Val Lys Glu
             340

<210> SEQ ID NO 23
<211> LENGTH: 331
<212> TYPE: PRT
<213> ORGANISM: Brassica napus

<400> SEQUENCE: 23

Met Ser Asn Val Thr Ala Asp Pro Thr Ala Asp Gly Pro Ser Thr Ala
 1               5                   10                  15

Val Ala Val Ser Asn Ser Thr Ala Ile Gln Thr Ser Pro Pro Thr Asp
                 20                  25                  30
```

-continued

```
Arg Pro Val Arg Val Tyr Ala Asp Gly Ile Tyr Asp Leu Phe His Phe
         35                  40                  45

Gly His Ala Arg Ser Leu Glu Gln Ala Lys Lys Ser Phe Pro Asn Thr
 50                  55                  60

Tyr Leu Leu Val Gly Cys Cys Asn Asp Glu Thr Thr His Lys Tyr Lys
 65                  70                  75                  80

Gly Arg Thr Val Met Thr Ala Glu Glu Arg Tyr Glu Ser Leu Arg His
                     85                  90                  95

Cys Lys Trp Val Asp Glu Val Ile Pro Asp Ala Pro Trp Val Ile Asn
                 100                 105                 110

Gln Glu Phe Leu Asp Asn His Arg Ile Asp Tyr Val Ala His Asp Ser
             115                 120                 125

Leu Pro Tyr Ala Asp Thr Ser Gly Ala Gly Lys Asp Val Tyr Glu Phe
130                 135                 140

Val Lys Lys Val Gly Arg Phe Lys Glu Thr Met Arg Thr Glu Gly Ile
145                 150                 155                 160

Ser Thr Ser Asp Ile Ile Met Arg Ile Val Lys Asp Tyr Asn Gln Tyr
                 165                 170                 175

Val Met Arg Asn Leu Asp Arg Gly Tyr Ser Arg Glu Asp Leu Gly Val
             180                 185                 190

Ser Phe Val Lys Glu Lys Arg Leu Arg Val Asn Met Arg Leu Lys Lys
         195                 200                 205

Leu Gln Glu Arg Val Lys Glu Gln Glu Lys Val Gly Glu Lys Ile
     210                 215                 220

Gln Thr Val Lys Met Leu Arg Asn Glu Trp Val Glu Asn Ala Asp Arg
225                 230                 235                 240

Trp Val Ala Gly Phe Leu Glu Ile Phe Glu Glu Gly Cys His Lys Met
                 245                 250                 255

Gly Thr Ala Ile Arg Asp Arg Ile Gln Glu Arg Leu Ile Arg Gln Ile
             260                 265                 270

Pro Arg Asn Arg Leu Glu Asn Gly Gln Asp Asp Thr Asp Asp Gln
         275                 280                 285

Phe Tyr Glu Glu Tyr Phe Asp His Asp Met Gly Ser Asp Glu Asp Glu
290                 295                 300

Glu Glu Arg Tyr Tyr Asp Glu Glu Glu Asp Val Glu Glu Glu Lys Tyr
305                 310                 315                 320

Lys Thr Val Lys Pro Asp Ala Lys Asp Lys
                 325                 330

<210> SEQ ID NO 24
<211> LENGTH: 329
<212> TYPE: PRT
<213> ORGANISM: Brassica napus

<400> SEQUENCE: 24

Met Ser Asn Val Thr Ala Asp Pro Thr Thr Asp Gly Pro Ser Thr Ala
 1               5                  10                  15

Val Ala Val Ser Gly Ser Ala Ala Ile Gln Ala Ser Pro Pro Thr Asp
                 20                  25                  30

Arg Pro Val Arg Val Tyr Ala Asp Gly Ile Tyr Asp Leu Phe His Phe
         35                  40                  45

Gly His Ala Arg Ser Leu Glu Gln Ala Lys Lys Ser Phe Pro Asn Thr
 50                  55                  60

Tyr Leu Leu Val Gly Cys Cys Asn Asp Glu Thr Thr His Lys Tyr Lys
 65                  70                  75                  80
```

-continued

```
Gly Arg Thr Val Met Thr Ala Glu Glu Arg Tyr Glu Ser Leu Arg His
                85                  90                  95
Cys Lys Trp Val Asp Glu Val Ile Pro Asp Ala Pro Trp Val Ile Asn
            100                 105                 110
Gln Glu Phe Leu Asp Asn His Arg Ile Asp Tyr Val Ala His Asp Ser
        115                 120                 125
Leu Pro Tyr Ala Asp Thr Ser Gly Ala Gly Lys Asp Val Tyr Glu Phe
    130                 135                 140
Val Lys Lys Val Gly Arg Phe Lys Glu Thr Met Arg Thr Glu Gly Ile
145                 150                 155                 160
Ser Thr Ser Asp Ile Ile Met Arg Ile Val Lys Asp Tyr Asn Gln Tyr
                165                 170                 175
Val Met Arg Asn Leu Asp Arg Gly Tyr Ser Arg Glu Asp Leu Gly Val
            180                 185                 190
Ser Phe Val Lys Glu Lys Arg Leu Arg Val Asn Met Arg Leu Lys Lys
        195                 200                 205
Leu Gln Glu Arg Val Lys Glu Gln Gln Glu Lys Val Gly Glu Lys Ile
    210                 215                 220
Gln Thr Val Lys Met Leu Arg Asn Glu Trp Val Glu Asn Ala Asp Arg
225                 230                 235                 240
Trp Val Ala Gly Phe Leu Glu Ile Phe Glu Glu Gly Cys His Lys Met
                245                 250                 255
Gly Thr Ala Ile Arg Asp Ser Ile Gln Glu Arg Leu Ile Arg Gln Ile
            260                 265                 270
Pro Arg Lys Lys Leu Glu Asn Gly Glu Asp Asp Thr Asp Asp Gln
    275                 280                 285
Phe Tyr Glu Glu Tyr Phe Asp His Asp Met Gly Ser Asp Glu Asp Glu
    290                 295                 300
Asp Glu Arg Tyr Tyr Asp Glu Glu Asp Val Glu Glu Glu Lys Ser
305                 310                 315                 320
Val Lys Lys Asp Ala Gln Asp Asn Lys
                325

<210> SEQ ID NO 25
<211> LENGTH: 326
<212> TYPE: PRT
<213> ORGANISM: Brassica napus

<400> SEQUENCE: 25

Met Thr Asn Val Thr Gly Asp Arg Asn Gly Asp Gly Arg Ser Thr Ala
  1               5                  10                  15
Val Thr Glu Ser Ser Pro Ser Asp Pro Ile Arg Val Tyr Ala
             20                  25                  30
Asp Gly Ile Tyr Asp Leu Phe His Phe Gly His Ala Arg Ser Leu Glu
         35                  40                  45
Gln Ala Lys Lys Ser Phe Pro Asn Thr Tyr Leu Leu Val Gly Cys Cys
     50                  55                  60
Asn Asp Asp Thr Thr His Lys Tyr Lys Gly Lys Thr Val Met Asn Asp
 65                  70                  75                  80
Gln Glu Arg Tyr Glu Ser Leu Arg His Cys Lys Trp Val Asp Glu Val
                 85                  90                  95
Ile Pro Asp Ala Pro Trp Val Ile Asn Gln Glu Phe Leu Asp Lys His
            100                 105                 110
Arg Ile Ala Tyr Val Ala His Asp Ala Leu Pro Tyr Ala Asp Ala Ser
```

-continued

```
            115                 120                 125
Gly Ala Gly Lys Asp Val Tyr Glu Phe Val Lys Lys Val Gly Arg Phe
    130                 135                 140
Lys Glu Thr Lys Arg Thr Glu Gly Ile Ser Thr Ser Asp Ile Ile Met
145                 150                 155                 160
Arg Ile Val Lys Asp Tyr Asn Gln Tyr Val Met Arg Asn Leu Asp Arg
                165                 170                 175
Gly Tyr Ser Arg Glu Asp Leu Gly Val Ser Phe Val Lys Glu Lys Arg
                180                 185                 190
Leu Arg Val Asn Met Arg Leu Lys Leu Gln Glu Lys Val Lys Glu
            195                 200                 205
Gln Gln Glu Lys Val Gly Glu Lys Ile Gln Thr Val Lys Met Val Arg
    210                 215                 220
Asn Glu Trp Val Glu Asn Ala Asp Arg Trp Val Ala Gly Phe Leu Glu
225                 230                 235                 240
Met Phe Glu Glu Gly Cys His Lys Met Gly Thr Ala Ile Arg Asp Arg
                245                 250                 255
Ile Gln Glu Lys Leu Met Arg Gln Glu Ser Lys Glu Leu Leu Glu Lys
                260                 265                 270
Gly Gln Asn Gly Gln Arg Glu Asp Thr Glu Glu Gln Phe Tyr Glu Glu
            275                 280                 285
Tyr Phe Glu His Asp Ile Val Asp Ser Cys Glu Asp Asn Glu Asp Asp
    290                 295                 300
Glu Glu Glu Tyr Tyr Asp Glu Ile Glu Glu Gln Cys Ser Ser Ala Ser
305                 310                 315                 320
Lys Ala Leu Lys Ser Asn
                325
```

PLANT CHOLINE PHOSPHATE CYTIDYLYLTRANSFERASE

This application claims the benefit of U.S. Provisional Application No. 60/170,375, filed Dec. 13, 1999.

FIELD OF THE INVENTION

This invention is in the field of plant molecular biology. More specifically, this invention pertains to nucleic acid fragments encoding choline phosphate cytidylyltransferase in plants and seeds.

BACKGROUND OF THE INVENTION

Phosphatidylcholine (PC), phosphatidylethanolamine (PE), phosphatidylserine (PS), phosphatidylinositol (PI), phosphatidylglycerol (PG) and diphosphatidylglycerol (DPG) are among the major phospholipids found in plant tissues. The distribution of these lipids among the various organelles of different tissues and among different plants has been comprehensively studied. The pathways by which these lipids are synthesized have also been studied extensively but very few of the plant enzymes involved in these pathways have been purified or their corresponding genes cloned.

Choline phosphate cytidylyltransferase (also called CTP: choline phosphate cytidylyltransferase; E.C. 2.7.7.15) catalyzes the conversion of ethanolamine and choline phosphate to their respective CDP-aminoalcohols. Choline phosphate cytidylyltransferase is thought to regulate the flux through the CDP-choline pathway for PC biosynthesis. In animal and plant cell extracts the choline phosphate cytidylyltransferase enzymatic activity is found in the soluble and in the membrane fractions. It has been proposed that the animal and plant choline phosphate cytidylyltransferases are regulated by the lipid-promoted translocation of the enzyme from the cytosol to the endoplasmic reticulum (ER). In this scenario, the enzyme is inactive while in the cytosole and reversible phosphorylation results in binding to the ER membrane and activation of the enzyme.

cDNAs encoding the rat and yeast choline phosphate cytidylyltransferase proteins have been identified (Kalmar et al. (1990) *Proc. Natl. Acad. Sci. USA* 87:6029–6033; Tsukagoshi et al. (1987) *Eur. J. Biochem.* 169:477–486). Pea, rape, and castor bean cDNAs encoding choline phosphate cytidylyltransferases have also been identified (Jones et al. (1998) *Plant Mol. Biol.* 37:179–185; Nishida et al. (1996) *Plant Mol. Biol.* 31:205–211; Wang and Moore (1991) *Plant Physiol.* 96(suppl.):126). Comparison of the amino acid sequences of the rat and yeast choline phosphate cytidylyltransferase show a highly conserved central region surrounded by divergent amino- and carboxy-terminal domains.

SUMMARY OF THE INVENTION

The present invention concerns an isolated polynucleotide that encodes a first polypeptide of at least 60 amino acids having at least 90% identity based on the Clustal method of alignment when compared to a second polypeptide having an amino acid sequence selected from the group consisting of SEQ ID NOs:6, 8, 10, 16, and 22. The present furhter concerns an isoalted polynucleotide that encodes a third polypeptide of at least 210 amino acids having at least 90% identity based on the Clustal method of alignment when compared to a fourth polypeptide having an amino acid sequence selected from the group consisting of SEQ ID NOs:2, 4, 14, 18, and 20.

In a second embodiment the first polynucleotide comprises a nucleotide sequence selected from the group consisting of SEQ ID NOs:1, 3, 5, 7, 9, 11, 13, 15, 17, 19, and 21.

In a third embodiment, this invention concerns an isolated polynucleotide encoding a cholinephosphate cytidylyltransferase.

In a fourth embodiment, this invention relates to an isolated complement of the polynucleotide of the present invention, wherein the complement and the polynucleotide consist of the same number of nucleotides and the nucleotide sequence and the complement share 100% complementarity.

In a fifth embodiment, the present invention concerns an isolated polynucleotide that comprises at least 180 nucleotides and remains hybridized to the isolated first polynucleotide of the present invention under a wash condition of 0.1×SSC, 0.1% SDS, and 65° C.

In a sixth embodiment, the invention also relates to a cell comprising an isolated polynucleotide of the present invention. The cell may be a yeast cell, a bacterial cell, or a plant cell. The plant cell may be regenerated into a transgenic plant.

In a seventh embodiment, the invention concerns a method for transforming a cell comprising introducing into a cell the first polynucleotide of the present invention and regenerating a plant from the transformed plant.

In an eighth embodiment, the invention relates to a first isolated polypeptide of at least 60 amino acids having at least 90% identity based on the Clustal method of alignment when compared to a second polypeptide having an amino acid sequence selected from the group consisting of SEQ ID NOs:6, 8, 10, 16, and 22. The invention further relates to a third isolated polypeptide of at least 210 amino acids having at least 90% identity based on the Clustal method of alignment when compared to a fourth polypeptide having an amino acid sequence selected from the group consisting of SEQ ID NOs:2, 4, 14, 18, and 20. The isolated polypeptide may have a sequence selected from the group consisting of SEQ ID NOs:2, 4, 6, 8, 10, 14, 16, 18, 20, and 22, and may encode a cholinephosphate cytidylyltransferase.

In a ninth embodiment, the invention concerns a chimeric gene comprising an isolated polynucleotide of the present invention operably linked to at least one regulatory sequence.

In a tenth embodiment, this invention relates to a method of altering the level of a cholinephosphate cytidylyltransferase in a host cell, the method comprising: (a) transforming a host cell with a chimeric gene of the present invention; and (b) growing the transformed host cell under conditions that are suitable for expression of the chimeric gene wherein expression of the chimeric gene results in altered levels of the cholinephosphate cytidylyltransferase in the transformed host cell.

A further embodiment.of the instant invention is a method for evaluating at least one compound for its ability to inhibit the activity of a cholinephosphate cytidylyltransferase, the method comprising the steps of: (a) transforming a host cell with a chimeric gene comprising a nucleic acid fragment encoding a cholinephosphate cytidylyltransferase polypeptide, operably linked to suitable regulatory sequences; (b) growing the transformed host cell under conditions that are suitable for expression of the chimeric gene wherein expression of the chimeric gene results in production of cholinephosphate cytidylyltransferase in the transformed host cell; (c) optionally purifying the cholinephosphate cytidylyltransferase polypeptide expressed by the transformed host cell; (d) treating the cholinephosphate cytidylyltransferase polypeptide with a compound to be tested; and (e) comparing the activity of the cholinephosphate cytidylyltransferase polypeptide that has been treated with a test compound to the activity of an untreated cholinephosphate cytidylyltransferase polypeptide, and selecting compounds with potential for inhibitory activity.

BRIEF DESCRIPTION OF THE DRAWING AND SEQUENCE LISTINGS

The invention can be more fully understood from the following detailed description and the accompanying Drawing and Sequence Listing which form a part of this application.

FIG. 1 depicts an alignment of the cholinephosphate cytidylyltransferase from the corn contig assembled from clones cbn10.pk0039.g12, cc71se-b.pk0025.g3, cco1n.pk058.p11, chpc24.pk0001.d1, cpf1c.pk008.o17, cph1c.pk001.o9, cr1n.pk0094.e10, p0010.cbpcm55r, p0014.ctutl75r, p0016.ctsau28r, p0018.chsst50r, p0037.crwax43r, p0068.clsah01r, p0105.camaq62r, p0110.cgsnv50r, and p0127.cntba77r (SEQ ID NO:2), soybean clone sfl1.pk130.e11 (SEQ ID NO:8), corn clone cbn10.pk0039.g12:fis (SEQ ID NO:12), the corn contig assembled of clones cen3n.pk0001.a4, cpe1c.pk003.p14, cr1n.pk0109.c11, cs1.pk0036.b7, p0121.cfrna59r, and p0128.cpiap69r (SEQ ID NO:14), rice clone rds3c.pk001.m16 (SEQ ID NO:16), rice clone rls6.pk0085.g3:fis (SEQ ID NO:18), the soybean contig assembled from PCR and clone sdp4c.pk014.b3 (SEQ ID NO:20), the wheat contig assembled from PCR and clone wlk8.pk0002.a5:fis (SEQ ID NO:22) with the *brassica napus* cholinephosphate cytidylyltransferases having NCBI General Identifier No. 7488484 (SEQ ID NO:23), 7488483 (SEQ ID NO:24), and 7488446 (SEQ ID NO:25). Amino acids conserved among all sequences are indicated by an asterisk (*) below the alignment. The amino acids corresponding to the catalytic core are underlined, and the putative HXGH motif is written in white and boxed in black. Dashes are used by the program to maximize the alignrnent.

Table 1 lists the plant source of the polynucleotides described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

| Cholinephosphate Cytidylyltransferase | | | |
|---|---|---|---|
| | | SEQ ID NO: | |
| Plant | Clone Designation | (Nucleotide) | (Amino Acid) |
| Corn | Contig of: cbn10.pk0039.g12 cc71se-b.pk0025.g3 cco1n.pk058.p11 chpc24.pk0001.d1 cpf1c.pk008.o17 cph1c.pk001.o9 cr1n.pk0094.e10 p0010.cbpcm55r p0014.ctutl75r p0016.ctsau28r p0018.chsst50r p0037.crwax43r p0068.clsah01r p0105.camaq62r p0110.cgsnv50r p0127.cntba77r | 1 | 2 |
| Rice | rls6.pk0085.g3 | 3 | 4 |
| Soybean | sdp4c.pk014.b3 | 5 | 6 |
| Soybean | sfl1.pk130.e11 | 7 | 8 |
| Wheat | wlk8.pk0002.a5 | 9 | 10 |
| Corn | cbn10.pk0039.g12:fis | 11 | 12 |
| Corn | Contig of: cen3n.pk0001.a4 cpe1c.pk003.p14 cr1n.pk0109.c11 cs1.pk0036.b7 p0121.cfrna59r p0128.cpiap69r | 13 | 14 |
| Rice | rds3c.pk001.m16 | 15 | 16 |
| Rice | rls6.pk0085.g3:fis | 17 | 18 |
| Soybean | PCR + sdp4c.pk014.b3 | 19 | 20 |
| Wheat | PCR + wlk8.pk0002.a5:fis | 21 | 22 |
| *Brassica napus* | NCBI GI No. 1418127 | | 23 |
| *Brassica napus* | NCBI GI No. 1418125 | | 24 |
| *Brassica napus* | NCBI GI No. 1416514 | | 25 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 180 contiguous nucleotides derived from SEQ ID NOs:1, 3, 5, 7, 9, 11, 13, 15, 17, 19, and 21, or the complement of such sequences.

The term "isolated" referes to materials, such as a nucleic acid moleucles and proteins, which are substantially free from components that normally accompany or interact with said materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamnic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 180 contiguous nucleotides derived from a nucleotide sequence selected from the group consisting of SEQ ID NOs:1, 3, 5, 7, 9, 11, 13, 15, 17, 19, and 21, and the complement of such nucleotide sequences may be used in methods of selecting an isolated polynucleotide that affects the expression of a cholinephosphate cytidylyltransferase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without an effect on the amino acid sequence of the encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normnally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a nucleotide sequence encoding a polypeptide of at least 60 amino acids having at least 90% identity based on the Clustal method of alignment when compared to a polypeptide selected from the group consisting of SEQ ID NOs:6, 8, 10, 16, and 22; (b) a nucleotide sequence encoding a polypeptide of at least 210 amino acids having at least 90% identity based on the Clustal method of alignment when compared to a polypeptide selected from the group consisting of SEQ ID NOs:2, 4, 12, 14, 18, and 20; and (c) a nucleotide sequence comprising the complement of (a) or (b).

The present invention refers to a nucleotide sequence comprising a nucleic acid sequence selected from the group consisting of SEQ ID NOs:1, 3, 5, 7, 9, 11, 13, 15, 17, 19, and 21.

Nucleic acid fragments encoding at least a portion of several cholinephosphate cytidylyltransferases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other cholinephosphate cytidylyltransferases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, and 21 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a cholinephosphate cytidylyltransferase polypeptide, preferably a substantial portion of a plant cholinephosphate cytidylyltransferase polypeptide, comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs:1, 3, 5, 7, 9, 11, 13, 15, 17, 19, and 21, and the complement of such nucleotide sequences; and amplifying a nucleic acid fragment (preferably a cDNA inserted in a cloning vector) using the oligonucleotide primer. The amplified nucleic acid fragment preferably will encode a portion of a cholinephospbate cytidylyltransferase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) Adv. Immunol. 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of phosphatidylcholine and phosphatidylethanolamine in those cells. This will be useful for creating oils with different characteristics. Since choline phosphate cytidylyltransferase is a key regulatory enzyme in phosphatidylcholine biosynthesis by the nucleotide (aminoalcohol) pathway, it may be used to identify products which may act as crop protection chemicals.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide selected from the group consisting of a polypeptide of at least 60 amino acids having at least 90% identity based on the Clustal method of alignment when compared to a polypeptide selected from the group consisting of SEQ ID NOs:6, 8, 10, 16, and 22 and a polypeptide of at least amino acids that has at least 210 amino acids having at least 90% identity based on the Clustal method of alignment when compared to a polypeptide selected from the group consisting of SEQ ID NOs:2, 4, 12, 14, 18, and 20.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded cholinephosphate cytidylyltransferase. An example of a vector for high level expression of the instant polypeptides in a bacterial host is provided (Example 6).

Additionally, the instant polypeptides can be used as targets to facilitate design and/or identification of inhibitors of those enzymes that may be useful as herbicides. This is desirable because the polypeptides described herein catalyze a key step in phosphatidylcholine biosynthesis by the nucleotide (aminoalcohol) pathway. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Composition of cDNA Libraries, Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
| --- | --- | --- |
| cbn10 | Corn Developing Kernel (Embryo and Endosperm); 10 Days After Pollination | cbn10.pk0039.g12 |
| cc71se-b | Corn Callus Type II Tissue, Somatic Embryo Formed | cc71se-b.pk0025.g3 |
| cco1n | Corn Cob of 67 Day Old Plants Grown in Green House[a] | cco1n.pk058.p11 |
| chpc24 | Corn 8 Day Old Shoot Treated 24 Hours With PDO Herbicide[b] | chpc24.pk0001.d1 |
| cen3n | Corn Endosperm 20 Days After Pollination[a] | cen3n.pk0001.a4 |
| cpe1c | Corn pooled BMS treated with chemicals related to phosphatase[c] | cpe1c.pk003.p14 |
| cpf1c | Corn pooled BMS treated with chemicals related to protein synthesis[d] | cpf1c.pk008.o17 |
| cph1c | Corn pooled BMS treated with chemicals related to redox ratio[e] | cph1c.pk001.o9 |
| cr1n | Corn Root From 7 Day Old Seedlings[a] | cr1n.pk0109.c11 |
| cr1n | Corn Root From 7 Day Old Seedlings[a] | cr1n.pk0094.e10 |
| cs1 | Corn Leaf Sheath From 5 Week Old Plant | cs1.pk0036.b7 |
| p0010 | Corn Log Phase Suspension Cells Treated With A23187[f] to Induce Mass Apoptosis | p0010.cbpcm55r |
| p0014 | Corn Leaves 7 and 8 from Plant Transformed With G-protein Gene, C. heterostrophus Resistant | p0014.ctutl75r |
| p0016 | Corn Tassel Shoots (0.1–1.4 cm), Pooled | p0016.ctsau28r |
| p0018 | Corn Seedling After 10 Day Drought, Heat Shocked for 24 Hours, Harvested After Recovery at Normal Growth Conditions for 8 Hours | p0018.chsst50r |
| p0037 | Corn V5[g] Stage Roots Infested With Corn Root Worm | p0037.crwax43r |
| p0068 | Corn Pericarp 28 Days After Pollination | p0068.clsah01r |
| p0105 | Corn V5[7] Stage Roots[a] | p0105.camaq62r |
| p0110 | Corn (Stages V3/V4[7]) Leaf Tissue Minus Midrib Harvested 4 Hours, 24 Hours and 7 Days After Infiltration With Salicylic Acid, Pooled[a] | p0110.cgsnv50r |
| p0121 | Corn Shank Ear Tissue Collected 5 Days After Pollination[a] | p0121.cfrna59r |
| p0127 | Corn Nucellus Tissue, 5 Days After Silking[a] | p0127.cntba77r |
| p0128 | Corn Primary and Secondary Immature Ear | p0128.cpiap69r |
| rds3c | Rice Developing Seeds From Top of the Plant | rds3c.pk001.m16 |
| rlr6 | Rice Leaf 15 Days After Germination, 6 Hours After Infection of Strain Magaporthe grisea 4360-R-62 (AVR2-YAMO); Resistant | rls6.pk0085.g3 |
| sdp4c | Soybean Developing Pods (10–12 mm) | sdp4c.pk014.b3 |
| sf11 | Soybean Immature Flower | sf11.pk130.e11 |
| wlk8 | Wheat Seedlings 8 Hours After Treatment With[h] | wlk8.pk0002.a5 |

[a]These libraries were normalized essentially as described in U.S. Pat. No. 5,482,845, incorporated herein by reference.
[b]Application of 2-[(2,4-dihydro-2,6,9-trimethyl[1]benzothiopyrano[4,3-c]pyrazol-8-yl)carbonyl]-1,3-cyclohexanedione S,S-dioxide; synthesis and methods of using this compound are described in WO 97/19087, incorporated herein by reference.
[c]Chemicals used included okadaic acid, cyclosporin A, calyculin A, cypermethrin
[d]Chemicals used included chloramphenicol, cyclohexamide, aurintricarboylic acid
[e]Chemicals used included diphenylene iodonium Cl, $H_2O_2$, paraquat, glutathione, N-acetyl-L-cysteine, aminotriazole
[f]A23187 is commercially available from several vendors including Calbiochem.
[g]Corn developmental stages are explained in the publication "How a corn plant develops" from the Iowa State University Coop. Ext. Service Special Report No. 48 reprinted June 1993.
[g]Application of 6-iodo-2-propoxy-3-propyl-4(3H)-quinazolinone; synthesis and methods of using this compound are described in U.S. Pat. No. 5,747,497, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pbluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the Saccharomyces cerevisiae Ty1 transposable element (Devine and Boeke (1994) Nucleic Acids Res. 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA sequences start towards the 3'-terminus of the gene. In order to obtain the upstream information one of two different protocols, which use two rounds of PCR amplification, are followed. The first of these methods results in the production of a fragment of DNA containing part of the desired gene while the second method results in the production of a gene containing the entire open reading frame for a certain gene. In the first round of amplification both methods use a vector-specific (forward) primer corresponding to a portion of the vector located at the 5'-terminus of the clone. In this round of amplification the first method uses a gene-specific primer complementary to a portion of the already known sequence and the second method uses a gene-specific primer complementary to a region of the 3'-untranslated sequence (also referred to as UTR). The second round of amplification uses, in both cases, a nested set of primers. Both methods are used to amplify fragments from one or more libraries or a randomly-chosen pool of libraries. Library pools are prepared using from 3 to 5 different libraries and normalized to a uniform dilution. The resulting PCR fragment is ligated into a pBluescript vector using commercial kits and following the manufacturer's protocol. These kits are available from several companies including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding choline phosphate cytidylyltransferases were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure BrookhaVen Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Choline phosphate Cgtidvlyltransferase

The BLASTX search using the EST sequence from clones listed in Table 3 revealed similarity of the polypeptides encoded by the cDNAs to one *Pisum sativum*; and three *Brassica napus* choline phosphate cytidylyltransferases (NCBI General Identifier Nos. 1657382, 1418125, 1418127, and 1416514, respectively). Shown in Table 3 are the BLAST results for individual ESTs ("EST") or for contigs assembled from two or more ESTs ("Contig"):

TABLE 3

BLAST Results for Sequences Encoding Polypeptides Homologous to Choline phosphate Cytidylyltransferases

| Clone | Status | BLAST pLog Score to | | | |
|---|---|---|---|---|---|
| | | 1418127 | 1418125 | 1657382 | 1416514 |
| Contig of:<br>cbn10.pk0039.<br>g12<br>cc71se-b.pk0025.<br>g3<br>cco1n.pk058.p11<br>chpc24.pk0001.<br>d1<br>cpf1c.pk008.o17<br>cph1c.pk001.o9 | Contig | 141.00 | 140.00 | 114.00 | 140.00 |

TABLE 3-continued

BLAST Results for Sequences Encoding Polypeptides Homologous to Choline phosphate Cytidylyltransferases

| Clone | Sta-tus | BLAST pLog Score to | | | |
|---|---|---|---|---|---|
| | | 1418127 | 1418125 | 1657382 | 1416514 |
| cr1n.pk0094.e10 | | | | | |
| p0010.cbpcm55r | | | | | |
| p0014.ctutl75r | | | | | |
| p0016.ctsau28r | | | | | |
| p0018.chsst50r | | | | | |
| p0037.crwax43r | | | | | |
| p0068.clsah01r | | | | | |
| p0105.camaq62r | | | | | |
| p0110.cgsnv50r | | | | | |
| p0127.cntba77r | | | | | |
| rls6.pk0085.g3 | EST | 44.10 | 45.00 | 42.70 | 42.05 |
| sdp4c.pk014.b3 | EST | 83.22 | 83.22 | 109.00 | 84.30 |
| sf11.pk130.e11 | EST | 16.00 | 15.70 | 53.50 | 16.40 |
| wlk8.pk0002.a5 | EST | 25.50 | 24.30 | 17.52 | 16.40 |

The sequence of the entire cDNA insert in clones cbn10.pk0039.g12, rls6.pk0085.g3, sdp4c.pk014.b3, and wlk8.pk0002.a5 was determined. PCR was used to find the 5' terminus of clones sdp4c.pk014.b3 and wlk8.pk0002.a5, and further sequencing and searching of the DuPont proprietary database allowed the idenlification of other corn and rice clones encoding choline phosphlate cytidylyltransferases. The BLASTX search using the EST sequences from clones listed in Table 4 revealed similarly of the polypeptides encoded by the cDNAs to choline phosphate cytidylyltransferases from one *Pisum sativum* (NCBI General Identifier No. 1657382 or 7488791) and three *Brassica napus* (NCBI General Identifier Nos. 1418127, 1418125, 1416514 or 7488484, 7488483, 7488446). There are two NCBI General Identifier numbers for each sequence. This is probably due to the fact that the searches were done at different times during the year and the NCBI database is constantly being upgraded. The amino acid sequences are identical between 165738 and 7488791, between 1418127 and 7488484, between 1418125 and 7488483, and between 1416514 and 7488446. Shown in Table 4 are the BLAST results for individual ESTs ("EST"), or for sequences encoding an entire choline phosphate cytidylyttransferase derived frorm the sequences of the entire cDNA inserts comprising the indicated cDNA clones, contigs assembled from two or more ESTs, contigs of the entire cDNA insert in the indicated cDNA clone and PCR ("CGS"):

TABLE 4

BLAST Results for Sequences Encoding Polypeptides Homologous to Choline phosphate Cytidylyltransferases

| Clone | Sta-tus | BLAST pLog Score | | | |
|---|---|---|---|---|---|
| | | 7488791 | 7488484 | 7488483 | 7488446 |
| cbn10.pk0039.g12:fis[a] | CGS | 117.00 | 123.00 | 123.00 | 120.00 |
| Contig of: cen3n.pk0001.a4 cpe1c.pk003.p14 cr1n.pk0109.c11 cs1.pk0036.b7 p0121.cfrna59r p0128.cpiap69r | CGS | 109.00 | 110.00 | 108.00 | 107.00 |

TABLE 4-continued

BLAST Results for Sequences Encoding Polypeptides Homologous to Choline phosphate Cytidylyltransferases

| Clone | Sta-tus | BLAST pLog Score | | | |
|---|---|---|---|---|---|
| | | 7488791 | 7488484 | 7488483 | 7488446 |
| rds3c.pk001.m16 | EST | 85.50 | 86.52 | 86.52 | 86.00 |
| rls6.pk0085.g3:fis[a] | CGS | 117.00 | 118.00 | 119.00 | 116.00 |
| PCR + sdp4c.pk014.b3 | CGS | 124.00 | 123.00 | 123.00 | 124.00 |
| PCR + wlk8.pk0002.a5: fis | CGS | 116.00 | 118.00 | 117.00 | 116.00 |

[a]The BLAST search using these sequences revealed similarity to NCBI General Identifier Nos. 1657382, 1418127, 1418125, and 1416514.

Some of the amino acid sequences of the present invention contain a signal sequence and a mature protein. The amino acid sequence set forth in SEQ ID NO:2 contains a signal sequence (amino acids 1–23) and a mature protein (amino acids 24–349). The amino acid sequence set forth in SEQ ID NO:4 contains a signal sequence (amino acids 1–25) and a mature protein (amino acids 26–149). The amino acid sequence set forth in SEQ ID NO:12 contains a signal sequence (amino acids 1–23) and a mature protein (amino acids 24–349). The amino acid sequence set forth in SEQ ID NO:14 contains a signal sequence (amino acids 1–37) and a mature toxin (amino acids 38–328). The amino acid sequence set forth in SEQ ID NO:18 contains a signal sequence (amino acids 1–27) and a mature protein (amino acids 28–342). The amino acid sequence set forth in SEQ ID NO:20 contains a signal sequence (amino acids 1–45) and a mature toxin (amino acids 46–363). The amino acid sequence set forth in SEQ ID NO:22 contains a signal sequence (amino acids 1–20) and a mature toxin (amino acids 21–344).

The BLASTN search against the NCBI EST database revealed sequences with 98 to 100% identity to some of the sequences of the present invention. Nucleotides 681 through 1051 from the nucleotide sequence set forth in SEQ ID NO:1 are 97% identical to nucleotides 614 through 245 of the zea mays EST from the Schmidt lab having NCBI General Identifier No. 4874508. Nucleotides 107 through 447 from the nucleotide sequence set forth in SEQ ID NO:3 are 99% identical to nucleotides 61 through 401 from the *Oryza sativa* cDNA clone E61543_1 A having NCBI General Identifier No. 5004923. Nucleotides 690 through 1303 from the nucleotide sequence set forth in SEQ ID NO:11 are 98% identical to nucleotides 614 through 1 from the Schmidt lab *Zea mays* endosperm CDNA library sequence having NCBI General Identifier No. 4874508. Nucleotides 672 through 1239 from the nucleotide sequence set forth in SEQ ID NO:13 are 100% identical to nucleotides 578 through 1 from the Walbot Lab *Zea mays* root cDNA library sequence having NCBI General Identifier No. 5871198. Nucleotides 141 through 517 from the nucleotide sequence set forth in SEQ ID NO:17 are 99% identical to nucleotides 61 through 464 from the *Oryza sativa* cDNA clone E61543_1A having NCBI General Identifier No. 5004923. Nucleotides 313 through 907 from the nucleotide sequence set forth in SEQ ID NO:19 are 96% identical to nucleotides 9 through 603 of the GENOME SYSTEMS Glycine max cDNA clone having NCBI General Identifier No. 7588989.

FIG. 1 presents an alignment of the mature protein in the amino acid sequences set forth in SEQ ID NOs:2, 8, 12, 14, 16, 18, 20, and 22 and the *Brassica napus* CCT1, CCT2, and CCT4 sequences (NCBI General Identifier Nos. 1418127, 1418125, 1416514 or 7488484, 7488483, 7488446; SEQ ID NOs:23, 24, and 25). The amino acid sequences from SEQ ID NOs:4, 6, and 10 are not included independently in the figure since they are covered by the amino acid sequences found in SEQ ID NOs:18, 20, and 22, respectively. The amino acid sequence of SEQ ID NO:4 corresponds to amino acids 3 through 149 of SEQ ID NO:18; the amino acid sequence of SEQ ID NO:6 corresponds to amino acids 111 through 304 of amino acid sequence having SEQ ID NO:20; and the amino acid sequence of SEQ ID NO:10 corresponds to amino acids 244 through 330 of SEQ ID NO:22. In this figure the amino acids corresponding to the catalytic core as described by Kalmar et al. ((1990) *Proc. Natl. Acad. Sci. USA* 87:6029–6033) are inderlined. This region contains an HXGH motif (written in white and boxed in black) probably involved in binding of CTP by the enzyme (Veitch and Cornell (1996) *Biochemistry* 35:10743–10750).

The data in Table 5 represents a calculation of the percent identity of the amino acid sequences set forth in SEQ ID NOs:2, 4, 6, 8, 10, 12, 14, 16, 18, 20, and 22 and the *Brassica napus* CCT1, CCT2, ard CCT4 sequences NCBI General Identifier Nos. 1418127, 1418125, 1416514 or 7488484, 7488483, 7488446; SEQ ID NOs:23, 24, and 25).

TABLE 5

Percent Identity of Amino Acid Sequences Deduced From the Nucleotide Sequences of cDNA Clones Encoding Polypeptides Homologous to Choline phosphate Cytidylyltransferases

| | Percent Identity to | | |
|---|---|---|---|
| SEQ ID NO. | 1418127 or 7488484 | 1418125 or 7488483 | 1416514 or 7488446 |
| 2 | 63.1 | 63.5 | 61.3 |
| 4 | 47.7 | 48.3 | 44.3 |
| 6 | 83.5 | 83.0 | 84.5 |
| 8 | 65.4 | 64.4 | 63.5 |
| 10 | 60.5 | 59.3 | 54.7 |
| 12 | 63.1 | 63.5 | 61.3 |
| 14 | 57.0 | 56.1 | 55.2 |
| 16 | 81.3 | 81.3 | 81.3 |
| 18 | 61.3 | 61.7 | 59.8 |
| 20 | 68.9 | 68.4 | 69.0 |
| 22 | 62.5 | 62.6 | 61.0 |

Sequence alignments and percent identity calculations were performed using the Megalign program of the LASERGENE bioinformatics computing suite (DNASTAR Inc., Madison. Wis. Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. The amino acid sequence set forth in SEQ ID NO:2 is identical to the one set forth in SEQ ID NO:12. Sequence alignments and BLAST scores and probabilities indicate that the nucleic acid fragments comprising the instant cDNA clones encode a substantial portion of two rice, two soybean, and one wheat phosphate cytidylyltransferase isoforms as well as three entire corn, one entire rice, one entire soybean, and one entire wheat choline phosphate cytidylyltransferase isoforms. These sequences represent the first corn, rice, soybean, and wheat sequences encoding choline phosphate cytidylyltransferases known to Applicant.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 μm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroformn as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Choline Phosphate Cytidylyltransferase The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terninus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include P-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. Assays for choline phosphate cytidylyltransferase are presented by Weinhold and Feldman (1992) *Methods Enzymol.* 209:248–258.

What is claimed is:

1. An isolated polynucleotide comprising:
    (a) a nucleotide sequence encoding a polypeptide having choline phosphate cytidylyltransferase activity, wherein the amino acid sequence of the polypeptide and the amino acid sequence of amino acids 46–363 of SEQ ID NO:20 have at least 80% identity based on the Clustal alignment method, or
    (b) the complement of the nucleotide sequence, wherein the complement and the nucleotide sequence contain the same number of nucleotides and are 100% complementary.

2. The polynucleotide of claim 1, wherein the amino acid sequence of the polypeptide and the amino acid sequence of amino acids 46–363 of SEQ ID NO:20 have at least 85% identity based on the Clustal alignment method.

3. The polynucleotide of claim 1, wherein the amino acid sequence of the polypeptide and the amino acid sequence of amino acids 46–363 of SEQ ID NO:20 have at least 90% identity based on the Clustal alignment method.

4. The polynucleotide of claim 1, wherein the amino acid sequence of the polypeptide and the amino acid sequence of amino acids 46–363 of SEQ ID No:20 have at least 95% identity based on the Clustal alignment method.

5. The polynucleotide of claim 1, wherein the nucleotide sequence comprises the nucleotide sequence of nucleotides 186–1140 of SEQ ID NO:19.

6. The polynucleotide of claim 1, wherein the amino acid sequence of the polypeptide comprises the amino acid sequence of amino acids 46–363 of SEQ ID NO:20.

7. A vector comprising the polynucleotide of claim 1.

8. A recombinant DNA construct comprising the polynucleotide of claim 1 operably linked to a regulatory sequence.

9. A method for transforming a cell comprising transforming a cell with the polynucleotide of claim 1.

10. A cell comprising the recombinant DNA construct of claim 8.

11. A method for producing a plant comprising transforming a plant cell with the polynucleotide of claim 1 and regenerating a plant from the transformed plant cell.

12. A plant comprising the recombinant DNA construct of claim 8.

13. A seed comprising the recombinant DNA construct of claim 8.

* * * * *